United States Patent
Grandhi et al.

(10) Patent No.: US 12,360,102 B2
(45) Date of Patent: Jul. 15, 2025

(54) HIGH-THROUGHPUT ASSAY FOR CELL MIGRATION, CHEMOTAXIS, AND FUNCTION

(71) Applicant: GlaxoSmithKline Intellectual Property Development Limited, Stevenage (GB)

(72) Inventors: Taraka Sai Pavan Grandhi, Collegeville, PA (US); Aaron Tien-Hsin Cheng, Collegeville, PA (US); Jason Elliot Ekert, Collegeville, PA (US); Terrence Taelim Roh, Collegeville, PA (US)

(73) Assignee: GlaxoSmithKline Intellectual Property Development Limited (GB)

( * ) Notice: Subject to any disclaimer, the term of this patent is extended or adjusted under 35 U.S.C. 154(b) by 0 days.

(21) Appl. No.: 18/833,282

(22) PCT Filed: Jan. 26, 2023

(86) PCT No.: PCT/IB2023/050684
§ 371 (c)(1),
(2) Date: Jul. 25, 2024

(87) PCT Pub. No.: WO2023/144747
PCT Pub. Date: Aug. 3, 2023

(65) Prior Publication Data
US 2025/0116657 A1    Apr. 10, 2025

Related U.S. Application Data

(60) Provisional application No. 63/438,945, filed on Jan. 13, 2023, provisional application No. 63/304,083, filed on Jan. 28, 2022.

(51) Int. Cl.
*G01N 33/50* (2006.01)
*B01L 3/00* (2006.01)

(52) U.S. Cl.
CPC ........ *G01N 33/5029* (2013.01); *B01L 3/5027* (2013.01); *G01N 33/505* (2013.01);
(Continued)

(58) Field of Classification Search
CPC .............. G01N 33/5029; G01N 33/505; B01L 3/5027; B01L 2200/0694; B01L 2300/0654; B01L 2300/0816; B01L 2300/0864
See application file for complete search history.

(56) References Cited

U.S. PATENT DOCUMENTS

| | | | |
|---|---|---|---|
| 5,302,515 A * | 4/1994 | Goodwin, Jr. ......... | C12Q 1/025 435/288.5 |
| 6,238,874 B1 * | 5/2001 | Jarnagin ................ | C12M 41/46 436/514 |

(Continued)

FOREIGN PATENT DOCUMENTS

| CA | 2 503 186 A1 | 5/2004 |
|---|---|---|
| WO | WO 2017/091075 A1 | 6/2017 |

(Continued)

OTHER PUBLICATIONS

Lin Francis et al: "T cell chemotaxis in a simple microfluidic device", Lab on a Chip, Royal Society of Chemistry, UK, vol. 6, No. 11, Jan. 1, 2006 (Jan. 1, 2006), pp. 1462-1469, XP002497559, ISSN: 1473-0197, DOI: 10.1039/B607071J [retrieved on Sep. 4, 2006].

(Continued)

*Primary Examiner* — Brian J. Sines
(74) *Attorney, Agent, or Firm* — Donald Huddler; Sean Brock

(57) ABSTRACT

An assay system permits study of cell migration through tissue-relevant extracellular matrices under a chemokine gradient within a modular assay platform. Activated CD3+ T-cells were detected, quantified, and studied as they migrated towards chemokines (CXCL10 and CXCL12) and chemokine mimetics (CXCR3 agonist) using the assay system. Discovery of drugs, and the study of microenviron- (Continued)

ments, stimuli, and responding cells are facilitated by the assay system.

25 Claims, 26 Drawing Sheets

(52) U.S. Cl.
CPC .............. *B01L 2200/0694* (2013.01); *B01L 2300/0654* (2013.01); *B01L 2300/069* (2013.01); *B01L 2300/0816* (2013.01); *B01L 2300/0864* (2013.01)

(56) References Cited

U.S. PATENT DOCUMENTS

| | | | | |
|---|---|---|---|---|
| 6,632,619 | B1 * | 10/2003 | Harrison | B01L 3/5027 436/805 |
| 7,419,823 | B2 * | 9/2008 | Kirk | G01N 33/5064 435/287.8 |
| 2006/0003310 | A1 * | 1/2006 | Klauke | G01N 33/48728 435/4 |

FOREIGN PATENT DOCUMENTS

| | | |
|---|---|---|
| WO | WO 2017/216113 A2 | 12/2017 |
| WO | WO 2021/091388 A1 | 5/2021 |
| WO | WO 2022/258668 A1 | 12/2022 |

OTHER PUBLICATIONS

Ziqiu Tong et al: "Chemotaxis of Cell Populations through Confined Spaces at Single-Cell Resolution", PLOS ONE, vol. 7, No. 1, Jan. 18, 2012 (Jan. 18, 2012), p. e29211, XP055565164, DOI: 10.1371/journal.pone.0029211.
De Haan Luuk et al: "A Microfluidic 3D Endothelium-on-a-Chip Model to Study Transendothelial Migration of T Cells in Health and Disease", International Journal of Molecular Sciences, vol. 22, No. 15, Jul. 30, 2021 (Jul. 30, 2021), p. 8234, XP055837958, DOI: 10.3390/ijms22158234.
2023 Manual 2—lane 96 digitaal in a nutshell.
Kim, et al., Biological applications of microfluidic gradient devices, Integrative Biology 2010, 2, 584-603 Received Jun. 19, 2010, Accepted Sep. 17, 2010, DOI: 10.1039/c0ib00055h.
Liu, Y.; Ren, X.; Wu, J.; Wilkins, J.A.; Lin, F. T Cells Chemotaxis Migration Studies with a Multi-Channel Microfluidic Device. Micromachines 2022, 13, 1567. https://doi.org/10.3390/mi13101567#.
Satti, et al., Lab Chip, 2020, 20, 3096 Received Mar. 26, 2020, Accepted Jul. 29, 2020 DOI: 10.1039/d0lc00311e.
Wu, et al., A compact microfluidic system for cell migration studies, Biomed Microdevices (2014) 16:521-528, DOI 10.1007/s10544-014-9854-4.
Written Opinion of the International Searching Authority (ISA237) PCT/IB2023/050684.

* cited by examiner

| | WELL 1 | WELL 2 | WELL 4 |
|---|---|---|---|
| | | | 5 μL |
| STAGE 1 | WAIT FOR 2-3 MINUTES FOR CHANNELS TO FILL UP (ON ICE) | | |
| | 1 μL | 1 μL | |
| STAGE 2 | PREPARE FOR GELATION | | |

WELL 2, END OF STAGE 1    WELL 2, END OF STAGE 2

BEFORE MEDIA REMOVAL (REPRESENTATIVE IMAGE ONLY)

DAY 1 (30 MINUTES AFTER WITHDRAWAL OF WELL 2 CONTENTS)
10 KDa FITC DEXTRAN DIFFUSION 2In

REPLICATES (DAY 1)

DAY 5 AFTER WITHDRAWAL
10 KDa FITC DEXTRAN DIFFUSION 2In

HIGH-THROUGHPUT ASSAY FOR CELL MIGRATION, CHEMOTAXIS, AND FUNCTION

TECHNICAL FIELD OF THE INVENTION

This invention is related to the area of biological assays. In particular, it relates to bioassays for identification of potential therapeutic products.

BACKGROUND OF THE INVENTION

Cell migration is critical in establishing and maintaining human multicellular tissues. For example, the recruitment of T-cells is an important component in the inflammatory cascade of the body. Similarly, wound healing requires proper movements of cells to specific locations.

Numerous model systems are available to study cell migration and barrier function. These model systems play a vital role in the development of new medicines, understanding various diseases and understanding the toxic effects of agents.

One important aspect of study in model systems is chemotaxis, which is the movement of an organism or entity in response to a chemical stimulus. Chemotaxis constitutes one of the core properties of a migratory cell[1-5]. The response of immune cells to a chemotactic gradient within the extracellular matrix (ECM) governs those cells' migration and function into and out of tissue microenvironments[6-11]. Consequently, modulating the chemotaxis machinery permits the attraction or exclusion of desired immune cell type(s) from diseased tissue microenvironments. As a result controlling this modulation could result in useful therapeutic outcomes[12].

The majority of chemotaxis within the human body occurs within three-dimensional extracellular matrix spaces. However, conventional cellular assays that try to mimic this movement do not reflect this aspect of the in vivo situation. Conventional assays utilize TRANSWELL®-based platforms to perform chemotaxis experiments[13]. In a typical embodiment of a TRANSWELL® chemotaxis experiment, soluble chemotactic stimuli are placed at a higher concentration below a perforated TRANSWELL® membrane and the responding cells are placed above it. A concentration gradient is created from the lower chamber to the chamber above, causing cells to migrate across the membrane.

TRANSWELL® devices (Corning, Inc., Lowell, MA) provide an artificial permeable growth support that inserts into a well of a tissue culture plate. By culturing a polarized cell monolayer across the surface of the permeable growth support, it functions as a selective barrier to separate the apical and basolateral chambers of the tissue culture well.

While conventional in vitro assays are able to model chemotaxis, they fail to replicate the complexity of chemotaxis in vivo. Within tissues, chemotaxis largely occurs within the extracellular matrix (ECM) that is populated by multiple cell types and filled with diverse ECM proteins, all of which influence migratory cell responses and function[14,15].

Another 3D model system for studying cell migration utilizes a 3-channel ORGANOPLATE® device available from Mimetas B. V. (http://mimetas.com/products.php). ORGANOPLATE® devices are microfluidics-based culture plates that enable culturing and screening of a wide range of physiologically relevant organ and tissue models, without the obstruction of artificial membranes. In a typical use of the 3-channel ORGANOPLATE® device, the chemoattractant and the cells are added to separate channels and the device is rocked to perfuse the cells. The cells then migrate from one channel, into a second, central channel. In a typical use of the 3-channel ORGANOPLATE® device, the distance of maximum migration is short, because the migration is in the direction of the width of a channel, rather than the length. In a typical use, the length of the gradient is short, because the gradient is set up across the width of a channel, rather than across its length. The use of the 3-channel ORGANOPLATE® device presents certain drawbacks related to ease of use, throughput, and distances travelled by the cell under chemotactic gradient.

Mimetas also sells a two-channel version of the ORGANOPLATE®. This plate has been primarily used to create tubular structures such as proximal tubules and endothelial tubes where cells are rested upon ECM that is filled in one of the two channels. Further, the plate is primarily rocked to promote fluid flow essential for proper functioning and maturation of the tubular cell culture. Cells are also grown within the ECM gel to support spheroid formation or other 3D cell interactions/network formations. Cell morphology can then be assessed by phase contrast microscopy and immunostaining followed by fluorescent (confocal) microscopy. However, the two-channel version of the Mimetas plate is not used to perform chemotaxis studies. There is a need in the art for a high throughput, screening platform that allows study and modulation of 3D cell migration and function within native extracellular matrix environments and that permits the cells' natural interactions with different tissue-resident cell types[16,17]. Existing microfluidic models for studying chemotaxis and 3D cell migration either lack the throughput essential for industrial drug discovery and development applications or are too laborious to create and use[16-18] Accordingly, there is a continuing need in the art for a high throughput, screening platform that captures 3D cell migration through native-like ECM environments within high-throughput microfluidic plates, while also permitting an imaging-based readout.

SUMMARY OF THE INVENTION

According to one aspect, a method of assaying chemotaxis of a cell population is provided. An assay plate is provided that comprises a first two-channel microfluidics unit comprising a first channel and a second channel. The first channel comprises a first gel. The second channel comprises a second gel. The first channel comprises a well at each end and the second channel comprises a well at one end. The first gel in the first channel extends between wells at each end. The second gel in the second channel extends from the well at one end through a central window in which the first and second channels are in fluid communication over a distance. The central window is distal to the well of the second channel. A population of cells is added to a well of the assay plate that is at one end of the first channel; the well is proximal to the well of the second channel. A fluid medium is added to the well of the second channel and to the distal well of the first channel. A test substance is added to the distal well of the first channel. Location of the cells of the population within the central window is monitored as the cells traverse the first channel from the well containing the cells toward the well containing the test substance.

According to another aspect, a method of preparing assay plates is provided. A first channel of a first two-channel microfluidics unit is filled with a fluid mixture of collagen and extracellular matrix to create aligned collagen fibers within the first channel. A second channel of the two-channel microfluidics unit is filled with fluid extracellular matrix, thereby establishing fluid contact between the two channels. The two-channel microfluidics unit is incubated until the extracellular matrix has formed a gel.

According to yet another aspect, an assay plate for assaying chemotaxis of a cell population is provided. The assay plate comprises a first two-channel microfluidics unit comprising a first channel and a second channel. The first channel comprises a first gel and the second channel comprises a second gel. The first and second channels are in fluid communication over a central window.

These and other embodiments which will be apparent to those of skill in the art upon reading the specification provide the art with a high-throughput, assay for monitoring migration, chemotaxis and cell function with a multi-parametric read-out.

BRIEF DESCRIPTION OF THE DRAWINGS

(FIG. 1A) Singular microfluidic unit of 2-lane (2-channel) Mimetas ORGANOPLATE® device (labeled with well 1-well 4; 101-104). Note that these regions may be referred to as well 1-well 4; frame 1-4; or 101-104. Note that the section labeled "well 3" and called out as 103 in FIG. 1A is referred to in this document as the "central window. " (FIG. 1B) Consistent filling of all the microfluidic channels of the 2-lane (2-channel) Mimetas ORGANOPLATE® device. The star symbols correspond to wells 2 and 3 respectively and are expanded to the right side of the line drawing. Scale bar=1000 µm (FIG. 1C) Fluorescent signal within the observation window (well 3; central window; 103) after 1 hour and 12 hours of 2 mg/ml 10 kDa FITC-Dextran addition to well 4 (high hydrostatic pressure differential setting). Scale bar=1000 µm. (FIG. 1D) Percent gradient remaining after addition of 1 µM 10 kDa FITC-Dextran addition to well 4 in two different hydrostatic pressure differential setting.

(FIG. 2A) Changes were made to the pre-gel addition sequence to achieve aligned collagen fibers (ECM: 2 mg/ml collagen mixed with 10% matrigel GFR). (FIG. 2B) Three different assay arrangements were studied to understand the best arrangement for robust Activated CD3+ T-cell chemotaxis response. T-cell migration distances were analyzed and quantified at 120 hours after experimental initiation. Number of T-cells that migrated in assay arrangement #1 in response to 0 and 300 nM CXCL12 is shown. (FIG. 2C) Final assay arrangement to study activated CD3+ T-cell chemotaxis against multiple chemotactic stimuli. Direction of the gradient and resulting cell chemotaxis are shown. ****—$p<0.001$, t-test for statistical significance (FIG. 3A) Activated CD3+ T-cell chemotaxis (5000 and 10000 cells) response against CXCR3 agonist at 48 hours within end-to-end ECM filled 2-lane Mimetas ORGANOPLATE® device. T-cell migration length (5000 and 10000 cells) and number (10000 cells only) of activated CD3+ T-cells responding to chemotactic stimuli are shown (FIG. 3B). Activated CD3+ T-cell chemotaxis response against recombinant CXCL10 and CXCL12 at 96 hours within end-to-end ECM filled 2-lane Mimetas ORGANOPLATE® device. T-cell migration length is shown (FIG. 3C) Number of Activated CD3+ T-cells responding to chemotactic stimuli at 96 hours. Concentration vs responder numbers are shown. *—$p<0.05$, —$p<0.01$, *—$p<0.005$, ****—$p<0.001$ One-way ANOVA with Dunnett's correction for multiple comparisons.

DETAILED DESCRIPTION OF THE INVENTION

Figure 1A:
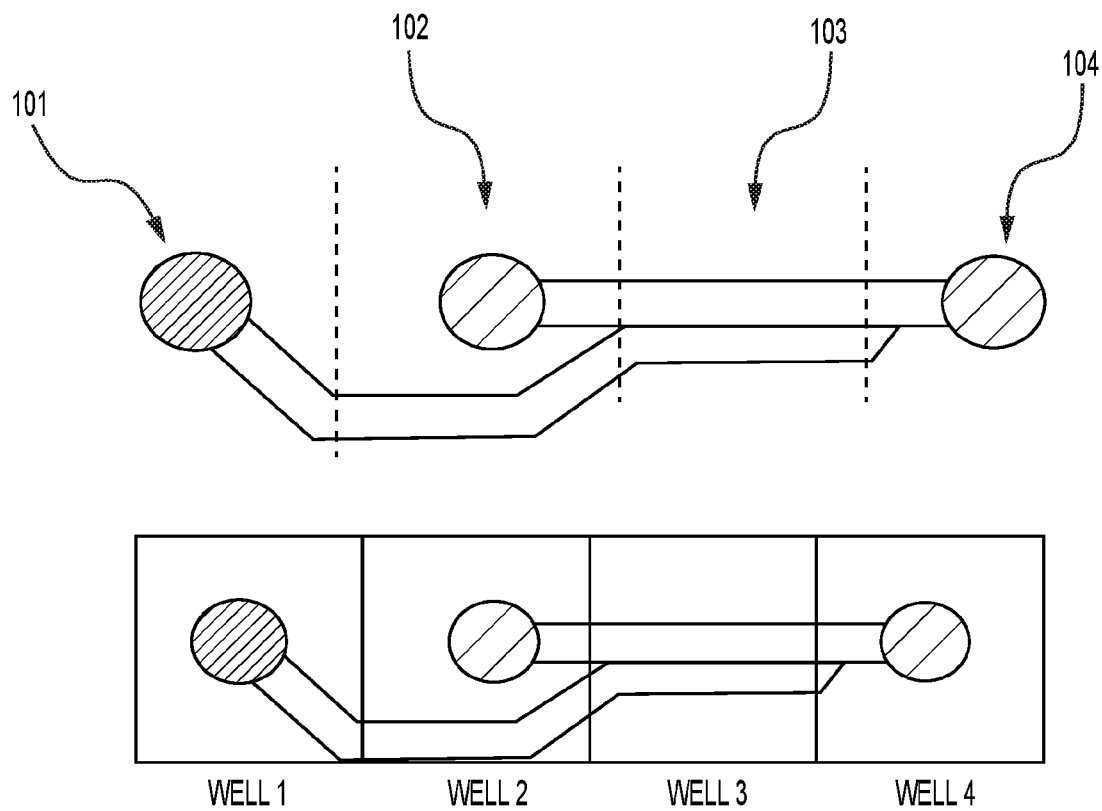
FIG. 1A-1D.

The inventors have developed a novel screening platform that captures 3D cell migration through native tissue-like extracellular matrix (ECM) environments within high-throughput microfluidic well plates with the ability to monitor the cells using confocal imaging.

Each of the channels of a 2-channel unit is filled with a gel or gel-forming precursor. The gel may be any that remains solid at cell culture temperature, generally between 30 and 42 degrees Centigrade. Examples of suitable gels or gel-forming precursors include without limitation native ECMs and cross-linked ECMs.

Additional substances which may be used as gels or gel-formers include: Matrigel™ solubilized basement membrane matrix secreted by Engelbreth-Holm-Swarm (EHS) mouse sarcoma cells, gelatin methacrylate (GelMA), synthetic ECMs such as polyethylene glycol based gels, alginate, porcine urinary bladder derived extra cellular matrix, peptide based hydrogels, MATRIGEL™ rgf, BME1, BMErgf, BME2, BME2rgf, BME3 (all MATRIGEL™ variants) Collagen I, Collagen IV, mixtures of Collagen I and IV, or mixtures of Collagen I and IV, and Collagen II and III), puramatrix, non-peptide based hydrogels, CellTak™, Collagen I, Collagen IV, MATRIGEL™ Matrix, Fibronectin, Gelatin, Laminin, Osteopontin, Poly-Lysine (PDL, PLL), PDL/LM and PLO/LM, PURAMATRIX®, Vitronectin, laminin, D-lysine, entactin, heparan sulfide proteoglycans, PLLA (poly-L-lactide), PLGA (poly(lactic-co-RECTIFIED SHEET (RULE 91) ISA/EP glycolic acid), and combinations thereof. The gels desirably fill the channels from end to end (well to well). To ensure that the gel fills from end to end, multiple applications of pre-gel may be added, for example if the volume of the gel is smaller than the volume of the pre-gel. In some embodiments other cell types (different from the cells whose chemotaxis is being assayed) are present in the gel during the assay. In some embodiments, additional protein or protein fibers are added to the gel. Such additions may be used, for example, to model a tissue environment more closely, to form internal structures to assist migration, or to alter the migration conditions to render them easier to observe or measure differences.

The first channel comprises a first gel. The second channel comprises a second gel. The first and second gels may be the same or different. The first channel comprises a well at each end and the second channel comprises a well at one end. The first gel in the first channel extends between wells at each end. The second gel in the second channel extends from the well at one end through a central window in which the first and second channels are in fluid communication over a distance. The central window is distal to the well of the second channel. Typically, the device comprises 2-channel microfluidics units only, without a third channel in each unit. Typically, the units comprise three wells, two on the first channel and one on the second channel. Other configurations may be used to enhance the setting up of a gradient, the distance of migration, the number of separate test substances being tested, etc.

Figure 2A:
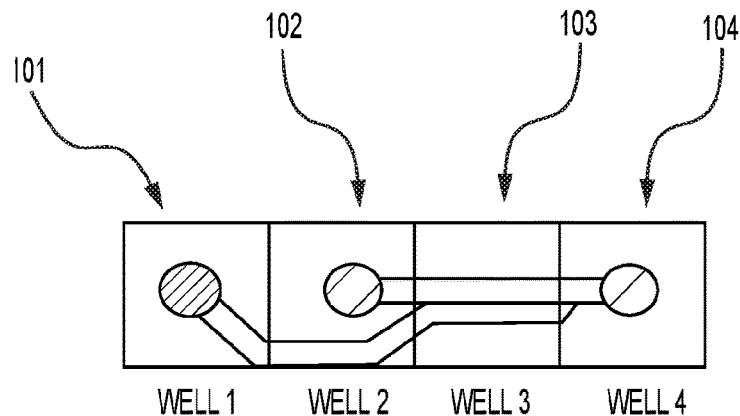
FIG. 2A-2C.
Figure 2A:
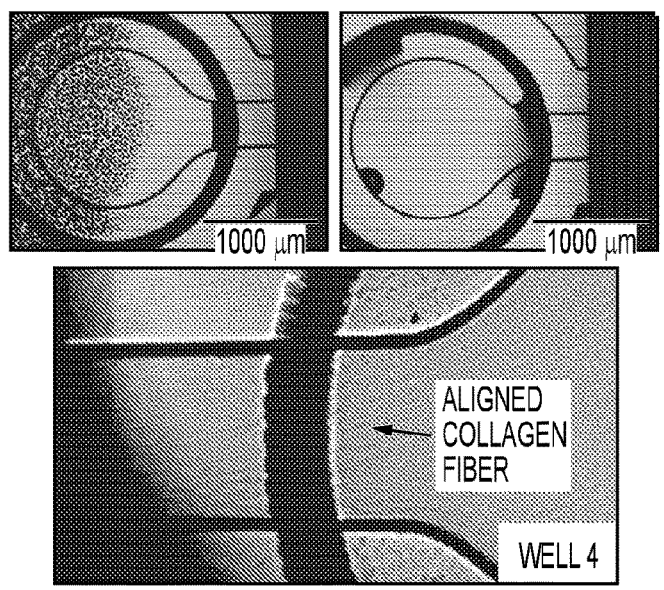

FIG. 2A illustrates frames 1-4 (101, 102, 103, and 104). The first channel runs between frames 2 and 4. The second channel runs between frame 1 and the central window (labeled as well 3 in FIG. 2A). Frame 1 corresponds to the single well connecting through the second channel to the central window. Frame 2 corresponds to the well at one end of the first channel, proximal to the well of the second channel. Frame 3 corresponds to the central window in which the two channels are in fluid communication. Observation of migration may be conveniently performed in this area, for example, using confocal microscopy or other label free imaging techniques. Frame 4 corresponds to the well at a second end of the first channel distal to frame 2 and distal to the well of the second channel (frame 1).

Figure 2B:
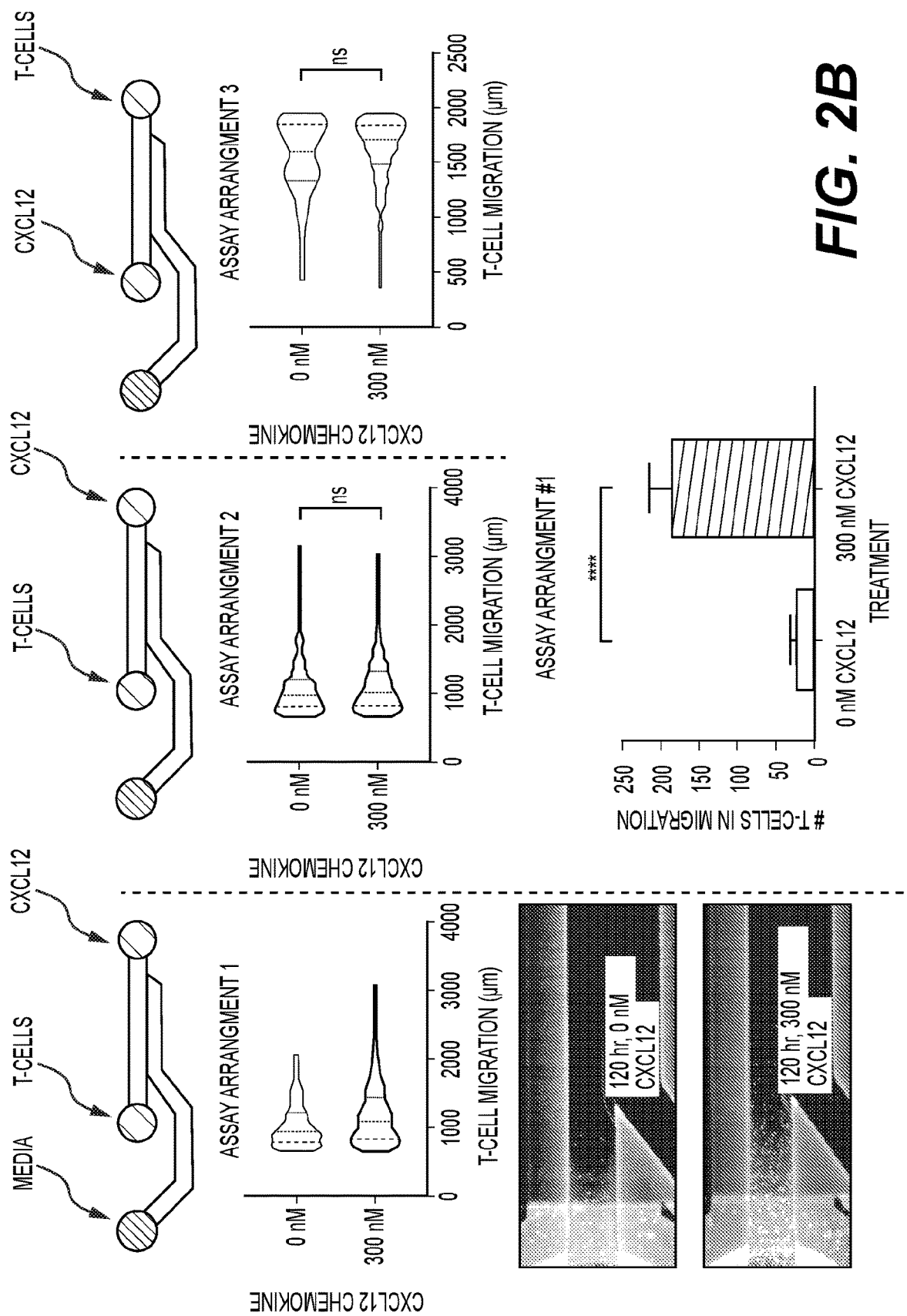
Figure 2C:
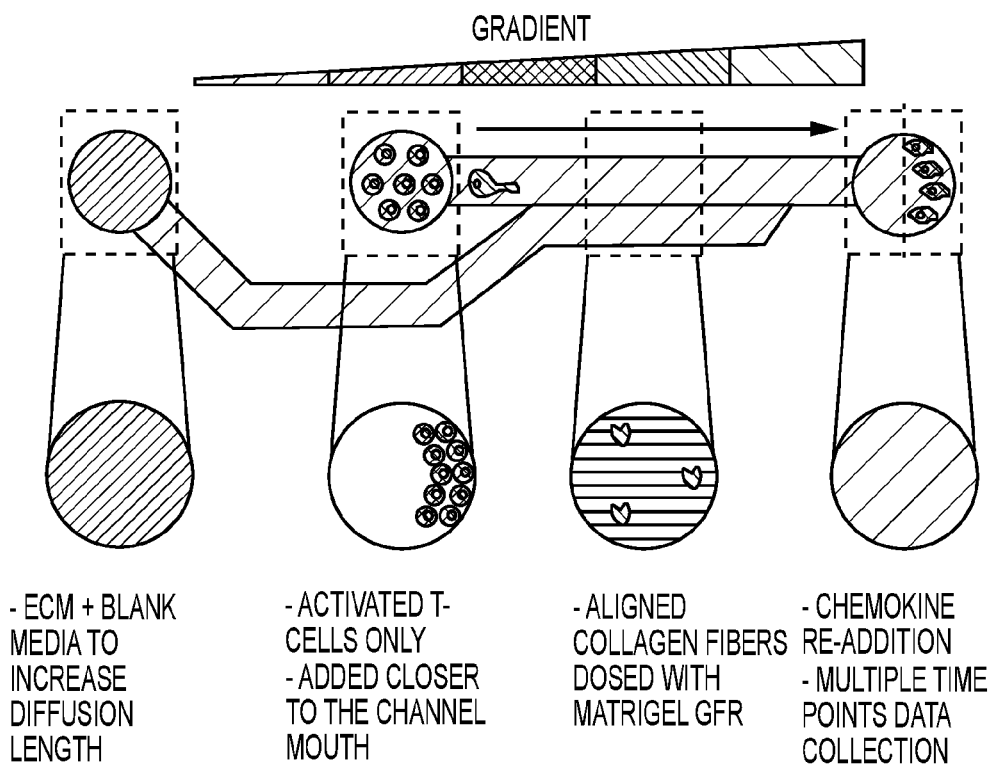

As shown in FIG. 2B, only the configuration where frame 1 comprises medium, frame 2 comprises cells, and frame 4 comprises chemoattractant provided statistically significant migration, reflecting a well set-up gradient of chemoattractant. Additional particular features of this assay configuration are shown in FIG. 2C. While not wanting to be bound by any particular theory of operation, the addition of media to well 1 (frame 1; 101) may function to increase the diffusion rate or length and push the chemoattractant deeper into well 2 (frame 2; 102). As shown in FIG. 2B, without media in well 1 (frame 1; 101), migration was not significant.

Types of medium/media suitable for use in the method include those that are appropriate for growth and maintenance of the cell type used in the assay. These include without limitation: RPMI 1640 (Roswell Park), DMEM (Dulbecco's Modification of Eagle's Medium), MEM (Minimum Essential Medium), HAM'S F-10 and F-12, and MEDIUM 199 (M199). Additional substances may optionally be included to increase growth and/or robustness of the cells. Such substances include without limitation growth factors, hormones, vitamins, salts, sugars, pH indicators, amino acids, etc.

In one particular embodiment, extracellular matrix of aligned collagen fibers blended with 10% matrigel growth factor reduced (GFR) can be used to fill both channels of a 2-lane Mimetas ORGANOPLATE® device unit separating migrating cells on one end and a chemotactic stimulus on another (with a linear migratory distance of more than 5 mm between them). Activated CD3+ T-cells stained with far-red nuclear stain responded to the chemokine gradient generated within the ECM by migrating into the microfluidic channel. Cell migration can be detected using confocal microscopy or other label-free imaging techniques. Types of confocal microscopy which may be used include laser scanning microscopy, spinning disk confocal microscopy, and programmable array microscopy (PAM). Other forms of detection may be used as is convenient for the particular assay. Other detection means include, but are not limited to widefield microscopy and fluorescence microscopy. In some embodiments cell migration is monitored using Simultaneous Label-free Autofluorescence Multi-harmonic imaging (SLAM). SLAM utilizes tissue and cellular properties to directly image live cell without exogenously added labels.[25] Using SLAM microscopy, a live, unprocessed chemotaxis assay can be imaged longitudinally to track cell metabolism of subject cells and 3D location via simultaneous acquisition of 2-photon autofluorescence, 3-photon autofluorescence, and third harmonic generation signal. Moreover, the second harmonic generation signal can provide visualization of the collagen fibers, enabling investigation of collagen fiber alignment and interaction with subject cells. Subject cells may be immune cells, T-cells, activated T-cells, CD3+ T-cells, macrophages, NK cells, or other immune cells as disclosed throughout the description. The activated CD3+ T-cells showed a concentration dependent chemotaxis into the ECM-filled microfluidic chambers across a wide array of chemotactic stimuli, such as recombinant chemokines and small molecule chemokine receptor agonists. This assay platform provides a physiologically relevant in-vitro assay. The assay allows studying and modulation of mammalian cell migration and function within a multicellular complex tissue microenvironment. For example, prior to adding the test cells in the well of frame 2, other cells can be grown in the gel of the first channel. The assay may be used, for example, to identify therapeutic agents, therapeutic adjuvants, and cellular sources of therapeutic agents.

In some embodiments, the population of cells which may be used to test migration and chemotaxis include immune cells, such as B and T lymphocytes, monocytic cells, and granulocytes. In some embodiments, the population of cells for use in the method include lymphocytes such as B cells, T cells or natural killer (NK) cells. Additionally, in some embodiments, specific lymphocyte subsets may be used, such as macrophages, CD4+ T cells, CD8+ T cells, regulatory T (Treg) cells, T follicular helper (Tfh) cells, naïve T cells, memory T cells, Th1 cells, Th2 cells, Th17 cells, or activated T cells, naïve B cells, memory B cells, transitional B cells, plasma B cells, CD56dim NK cells or CD56bright NK cells. In some embodiments, the population of cells of the method include monocytic cells such as monocytes, macrophages, dendritic cells, alveolar macrophage, microglia, or kupffer cells. In some embodiments, the population of cells of the method include granulocytes such as neutrophils, eosinophils, basophils and mast cells. In some embodiments, the population of cells of the method include engineered cells such as chimeric antigen receptor T (CAR- T) cells, T cells expressing engineered T cell receptors (TCRs), CAR-NK cells or CAR macrophages (CAR-M). In some embodiments, a population of cells previously subjected to different treatments are added to different proximal wells of the first channels. For example, in some embodiments, the populations of cells are pre-treated with therapeutic molecules such as proteins (e.g., antibodies), nucleic acids, or small organic molecules. In some embodiments, tumor cells or immortalized cells, such as Jurkat cells, may be used to study metastasis, for example. Immune cell migration toward tumor cells can be studied using immune cells in well/frame 2 and tumor cells in well/frame 4. Test substances can be added to well/frame 4 to identify those test substances which increase or decrease such migration.

The number of cells added to the proximal well of the first channel may be varied to evaluate chemotaxis in response to the test substance. For example, in some embodiments, about 1000 cells, about 5000 cells, or about 10000 cells are added to the proximal well of the first channel. The long range of gradient space through which migration may occur in the assay provides the opportunity to observe speed, distance, and cell number of migrating cells. Such observation may occur over an extended period of time, for example, between 1 and 10 days, between 2 and 9 days, between 3 and 8 days, or between 4 and 7 days. One means of observing migration involves confocal microscopy or other label free imaging techniques. Stains may be used to assess viability of cells. In addition, cells which stop moving within the gradient may indicate loss of viability. Supernatant collected from wells may, for example, be subjected to Multiplex Luminex assays for accurate cytokine analysis (cytokines of interest).

Test substances which may be used include without limitation small organic molecules, proteins, peptides, and nucleic acids. Test substances may be purified or unpurified extracts of natural products, in some instances. Test substances may be synthetic, semi-synthetic, or natural. Substances may be previously known to possess a therapeutic activity or not. In some embodiments, test substances include chemoattractants, chemorepellents, agonists of a chemoattractant receptor or antagonists of a chemoattractant. In some embodiments, chemoattractants include chemokines such as CCL1, CCL2, CCL3, CCL4, CCL5, CCL6, CCL7, CCL8, CCL9/CCL10, CCL11, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CX3CL1, XCL1, or XCL2. In some embodiments, agonists of a chemoattractant receptor are chemokines or small organic molecules. In some embodiments, the chemoattractant receptors include CCR1, CCR2, CCR3, CCR4, CCR5. CCR6, CCR7, CCR8, CCR9, CCR10, CXCR1, CXCR2, CXCR3, CXCR4, CXCR5, CXCR6, XCR1 or CX3CR1.

For example, in some embodiments, the test substance is a CXCR3 agonist. In some embodiments, the antagonists of a chemoattractant include small organic molecules, proteins (e.g. antibodies), peptides and nucleic acids. In some embodiments, different test substances are provided by different cell populations that make the test substance in situ.

The concentration of test substances used in the method may be varied to determine concentration-dependent effects on cell chemotaxis. In some embodiments, the concentration of the test substance is about 10 µM, about 5 µM, about 2.5 µM, about 1.25 µM, about 0.625 µM, about 0.3125 µM, about 0.15625 µM, about 0.075 µM, about 0.0375 µM, about 0.01875 µM, about 0.009375 µM or about 0.0046875 µM.

The methods of the invention may lead to a deeper insight and subsequent modulation of immune cell movement and function within tissues. These could result in novel therapeutic strategies against multiple categories of diseases, including in the fields of oncology, immune-oncology, auto-immune disorders, regenerative medicine, and neurodegenerative diseases[19-22] The art of high-throughput screening lacks assay platforms that match the throughput of traditional TRANSWELL™ plates and allow generation and monitoring of cell migration through native 3D complex tissue microenvironments[17]. The illustrated embodiment is an assay platform built within a 2-lane Mimetas ORGANOPLATE® device to study 3D cell migration in a throughput of 96 units within a 384 well plate. The assay arrangement could however accommodate more units such as 384 units within a 1536 well plate (leading to increased throughput). The assay platform built within the 2-lane Mimetas ORGANOPLATE® device enables the study of cell migration within the platform[23,24].

Other known microfluidic devices could be employed as is, or modified and to run the assays described here. For instance, known microfluidic devices are described in S. J. Trietsch, G. D. Israels, J. Joore, T. Hankemeier, P. Vulto, Microfluidic titer plate for stratified 3D cell culture, Lab Chip 2013, vol. 13, no. 18, pp. 3548-3554, Edinson Lucumi Moreno, Siham Hachi, Kathrin Hemmer, Sebastiaan J. Trietsch, Aidos S. Baumuratov, Thomas Hankemeier, Paul Vulto, Jens C. Schwamborn and Ronan M. T. Fleming, Differentiation of neuroepithelial stem cells into functional dopaminergic neurons in 3D microfluidic cell culture, Lab Chip, Vol. 15, No. 11, pp. 2419-2428, in WO2012120102 in WO201 4038943, in Mu et al, Lab on a Chip, 201 3, 13, 16 12-1 6 18, or in Jang et al, integr biol, 201 3, 5, 11 9.

Intentional pre-gel filling of the two channels of the 2-lane Mimetas ORGANOPLATE® creates an end-to-end ECM plug between two connected chambers, along with additional ECM footprint in all the wells, with migrating cells on one end and chemokine or other trigger in another. One or more cell types can migrate towards the chemokine gradient established within the ECM plug and be tracked via confocal microscopy or other label free imaging techniques. Other benefits of the proposed assay platform over traditional methods are outlined in Table 1, below.

TABLE 1

| | TRANSWELL ® Assay for chemotaxis | High-throughput 2-channel cell assay for chemotaxis |
| --- | --- | --- |
| 1 | TRANSWELL ® based cell migration assays (Incucyte assay) do not allow migration of immune cells through complex multi-cell, ECM rich tissue microenvironments | Quantifying 3D (>5 mm) cell (e.g., immune cell) migration (linear distance of 5 mm) through end-to-end ECM loaded channel that harbors defined chemokine gradient that can be refreshed at regular intervals to monitor migration in a higher throughput setting. |

TABLE 1-continued

| TRANSWELL ® Assay for chemotaxis | High-throughput 2-channel cell assay for chemotaxis |
|---|---|
| 2 Imaging difficulties at higher magnifications (Working distances) | Confocal microscopy or other label free imaging techniques capture at higher magnifications to truly study 3D chemotactic migration |
| 3 Difficult to distinguish between cell migration and cell death upon dosing with a therapeutic agent | Horizontal separation of wells that harbor migratory cells and chemokine stimulus. Chemokine producing cells could be cultured instead of adding the stimulus. Co-culture of desired cell types inside the ECM to understand migrating immune cell - tissue resident cell interaction Migratory cell stress/death can be monitored via stagnant/slow moving cells/counter stains No plate rocking needed allowing easier high-throughput screens Multi-parametric readout of chemotaxis (Speed and distance of migration within the ECM system) Achieves 96 well throughput similar to TRANSWELL ™ based assays |

Unlike the traditional use of the 2-lane Mimetas ORGANOPLATE®, the disclosed chemotaxis assays do not require plate rocking, resulting in faster and easier automation of the entire process[23, 24]. The platform also allows tracking of linear 3D cell migration through a window of over 5 mm of solid ECM gel in a 96 well throughput, unlike many other contemporary systems[13,18]. Additional cell types can also be added to the central ECM channel to closely mimic the tissue microenvironment through which the cell migration is observed. Further, the speed and distance of the migrating cell can be measured within the migration channel to achieve a multi-parametric readout of the migration process.

The assay provides a robust and reproducible platform to study cell migration. Some of the features that may be used are the inclusion of ECM in all the channels that are seamlessly connected together, aligned collagen fibers within the central migration channel, addition of cells close to the mouth of the channel, refreshing the chemokine or other attractant or test substance during the course of the assay period.

Overall, the disclosed assay provides a high-throughput, screening-amenable assay platform, fine-tuned to achieve and modulate robust chemotaxis and cell migration against a wide variety of stimuli, which can be imaged using confocal microscopy or other label free imaging techniques. The assay can be modified to incorporate increased complexity (such as combinations of cell types) to mimic better the native tissue types through which chemotaxis is desired.

The disclosed assay opposes cells and test substances at opposite ends of a single channel. In contrast, other assays may use separate channels for test substance and for cells. Additionally, such assays may use yet another channel between the two channels for test substance and for cells, through which test substance can set up a gradient through which cells may migrate. This may lead to a shorter distance across a channel (rather than along a channel) so that quantitative differences in migration/chemotaxis are more difficult to assess and distinguish.

The above disclosure generally describes the present invention. All references disclosed herein are expressly incorporated by reference. A more complete understanding can be obtained by reference to the following specific examples, which are provided herein for purposes of illustration only, and are not intended to limit the scope of the invention.

EXAMPLE 1

Materials

The following materials were purchased and used as per vendor's recommendation.

| Item | Catalog number | Lot number | Vendor |
|---|---|---|---|
| RPMI MEDIA | A42755SA | 2283927 | Hyclone |
| Purecol Collagen | 5074-35 ML | 8227 | Advanced Biomatrix |
| Matrigel Phenol free Growth factor reduced | 356231 | 104008 | Corning |
| 2-lane ORGANOPLATE | 9605-400B/ 9603-400B | 200916-42 | Mimetas |
| Heat inactivated FBS | 10100-147 | NA | Gibco |
| CXCL12 | 350-NS | AFV2720072 | R&D Systems |
| CXCL10 | 266-IP | KJ0719101 | R&D Systems |
| Nuclight Rapid Red dye | 4717 | 19NO213-041521 | Incucyte |
| 1X PBS | 14190-144 | 2235066 | Invitrogen |
| Ultrapure water | 10977-015 | 22777173 | Invitrogen |
| IDOT Pure plates 80-200 | 130-96001 | 200420-200-05 | CellInk |
| IL2 | 130-097-748 | 5200803868 | R&D Biosciences |
| T Cell TransAct | 130-111-160 | 5200709781 | Miltenyi |
| Peripheral Blood, Cryopreserved, CD3+ Pan T Cells, Negatively Selected, 25M | PB009-1F | | AllCells |

EXAMPLE 2

Methods

Figure 4:
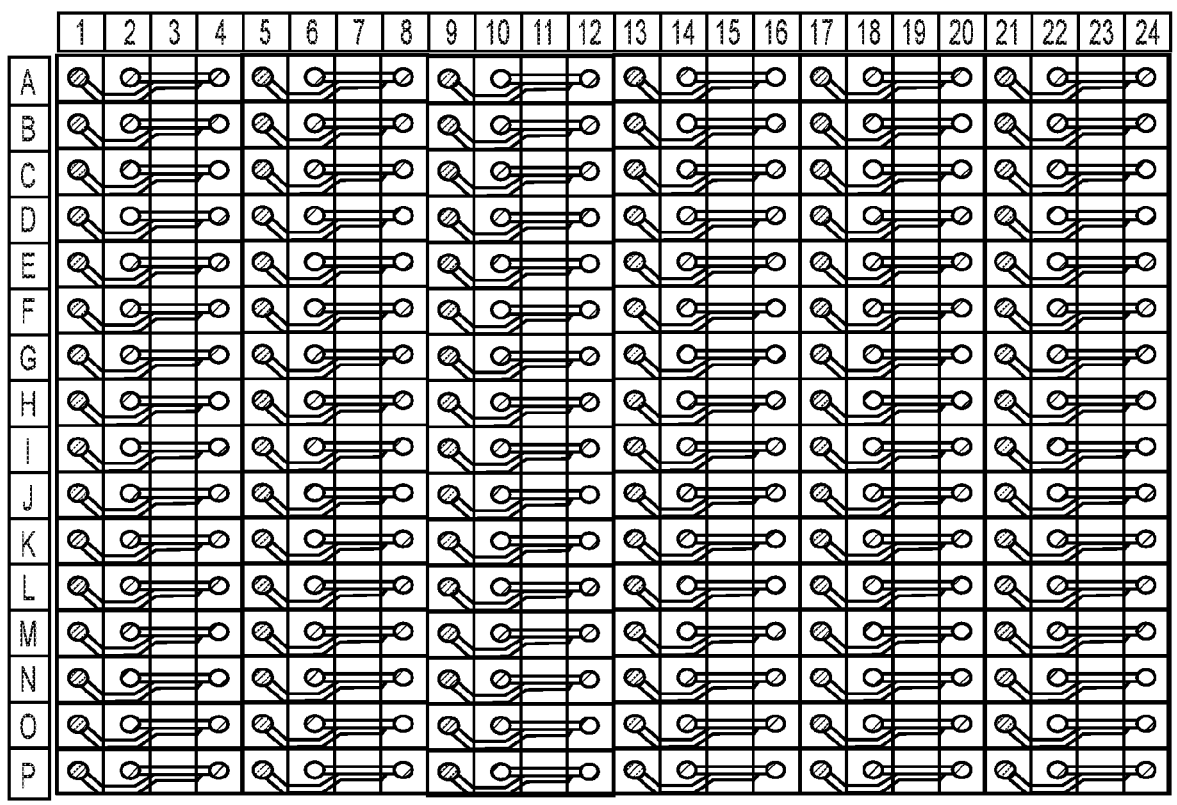
FIG. 4: 384-well plate lay out of 2-lane Mimetas ORGANOPLATE®. 96 units of the 2-lane microfluidic system are built within a 384 well plate geometry.
Figure 5:
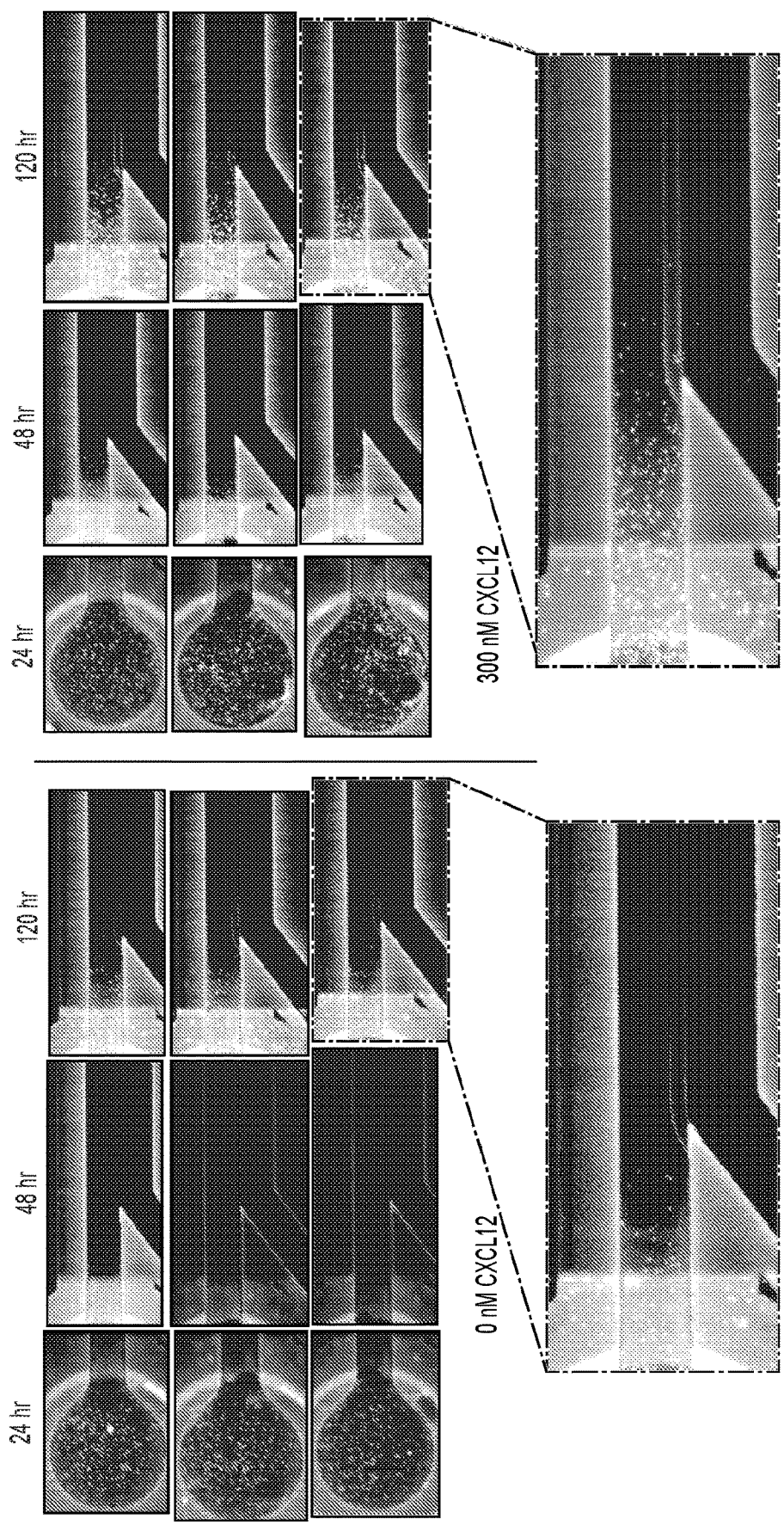
FIG. 5: Activated CD3+ T-cell migration response to 0 nM and 300 nM CXCL12 chemokine at 24, 48 and 120 hours. CXCL12 chemokine was refreshed at 48 hours. Data from three different replicates are shown.

Gel Loading into the 2-Lane Mimetas ORGANOPLATE®
50 µl of 37° C. warmed 1×PBS were added to wells in columns 3, 7, 11, 15, 19 and 23 observation windows of Mimetas 2-lane ORGANOPLATE® and stored at 4° C. 5 µl of ice-cold 2 mg/ml collagen mixed with 10% (v/v) of low endotoxin matrigel GFR were added to wells in columns 4, 8, 12, 16, 20 and 24 of chilled Mimetas 2-lane ORGANOPLATE® to potentially create aligned collagen fibers within the microfluidic channels. After the ECM filled all the 5 microfluidic channels, 1 µl of ice-cold ECM was quickly added to wells in columns 1, 2, 5, 6, 9, 10, 13, 14, 17, 18, 21, and 22 to allow for contact to be established between the ECM footprints. 4.5 ml of 37° C. warmed ultrapure water was added to both the ends of sterile MicroClime Environmental Lid and placed atop the Mimetas ORGANOPLATE®. The assembly was placed in a humidified 37° C. cell culture incubator for 45 minutes to ensure complete gelation of all the wells throughout the plate and used for the experiment. A model of Mimetas 2-lane ORGANOPLATE® is shown in FIG. 4.

Chemokine Addition and Cell Loading into Gel Filled 2-Lane Mimetas ORGANOPLATE®

After the gelation, 50 µl of blank media was added to the wells of columns 1, 5, 9, 13, 17 and 21 followed by 50 µl of the desired chemokine at different concentrations in wells of columns 4, 8, 12, 16, 20 and 24. 1:1000 (v/v) NUCLIGHT® Rapid Red dye stained and washed activated CD3+ T-cells were quickly added towards the mouth of the channel allowing increased deposition of cells closer to the mouth of the channel in the wells of column 2, 6, 10, 14, 18 and 22 in RPMI media with 0.5% FBS. CD3+ T-cells were activated for 48 hours prior the experiment with 1:500 (v/v) TRANSACT® beads with 20 IU/mL IL2 in RPMI media with 10% FBS. The ORGANOPLATE® was left undisturbed for 3-5 minutes to allow T-cell settling followed by placing them in humidified 37° C. incubator for the duration of the experiment. Chemokines were replaced as needed after 48 and 96 hours along with the 37° C. warmed ultrapure water within the sterile MicroClime Environmental Lid. A model of Mimetas 2-lane ORGANOPLATE® is shown in FIG. 4.

Imaging the Migrating Cells and Subsequent Analysis

Wells from columns 2, 3, 4, 6, 7, 8, 10, 11, 12, 14, 15, 16, 18, 19, 20, 22, 23 and 24 were imaged in the far red and bright field channels at 4× magnification on days 0, 1, 2, 3, 4, 5 and 6 using an INCELL™ 6500 confocal microscope to identify the cells within the migrating channel. Z-stack of six images at different focal planes 50 µm apart spanning the thickness of the microfluidic channel were captured followed by maximum projection to create a singular image of the migratory channel. Images were then transferred to COLUMBUS™ image segmentation software to extract the X-Y location of the migratory CD3+ T-cells within the microfluidic channel. Area cut-offs and positive signal over background were used to accurately identify the fluorescent T-cells over the background. A model of Mimetas 2-lane ORGANOPLATE® is shown in FIG. 4.

Data Analysis and Statistics

The X-Y data of the CD3+ T-cells was transferred to SPOTFIRE™ analytics platform for image representation. The X axis location of the migratory T-cells across 4 different replicate wells were pooled and represented as a horizontal violin plot using the GRAPHPAD™ prism. Kruskal-Wallis test for statistical significance was used to understand the significance of a chemokine concentration in driving increased migration distance into the end-to-end solid ECM channel over blank media controls. Replicates were individually compared amongst each other to ensure significance between the sample and replicate and the lowest significance difference was represented in the graph. The total number of cells migrating across the four replicates were represented as mean+/−SEM and one-way ANOVA with Dunnett's correction for multiple comparisons was used to understand the statistical significance of multiple chemokine concentrations over blank media controls.

EXAMPLE 3

End-to-End Gel Loading and FITC-Dextran Gradient Formation within 2-Lane Mimetas ORGANOPLATE®

Figure 1B:
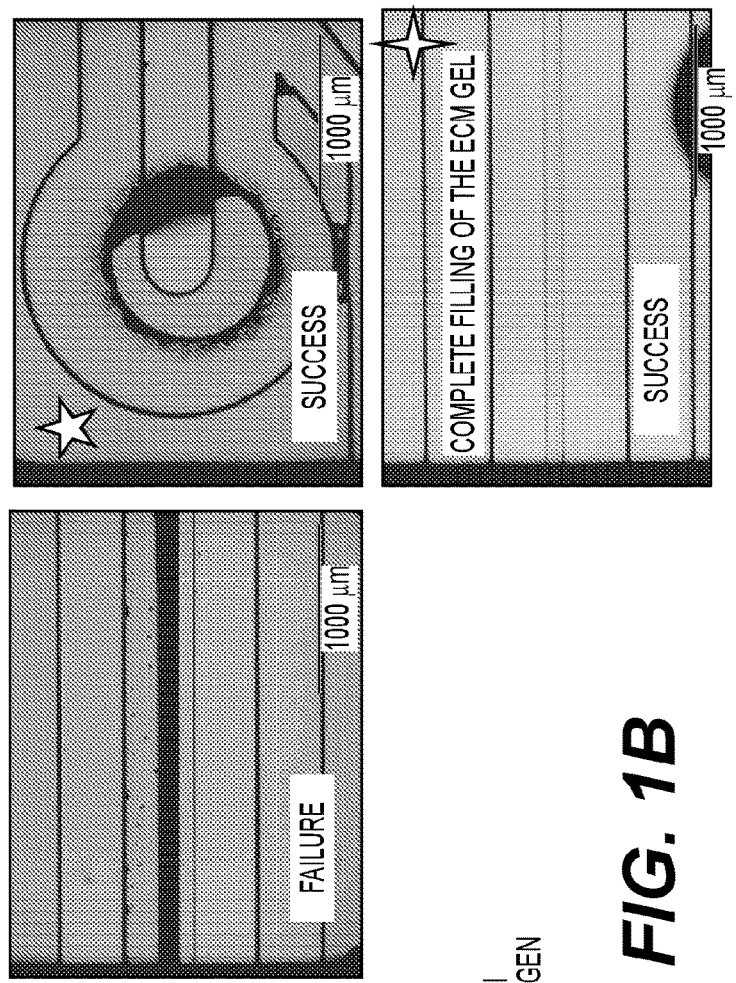
Figure 1B:
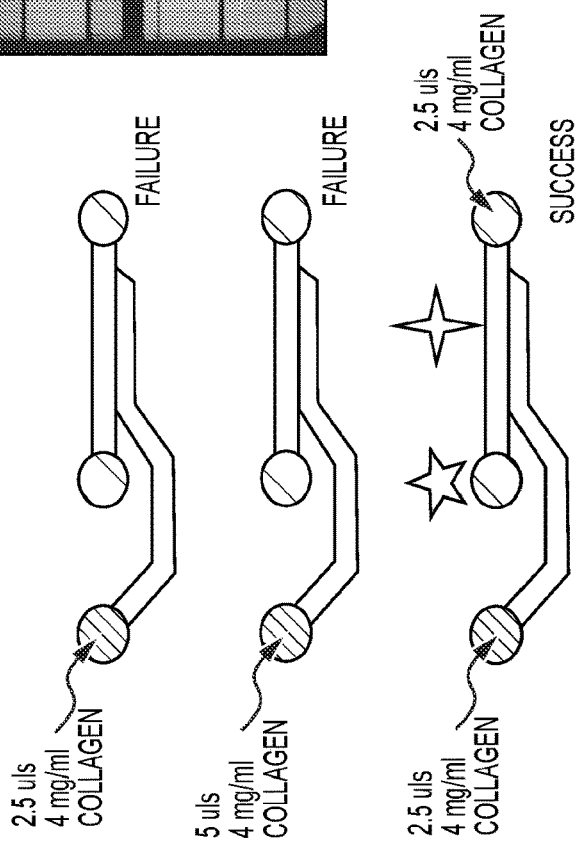
Figure 1C:
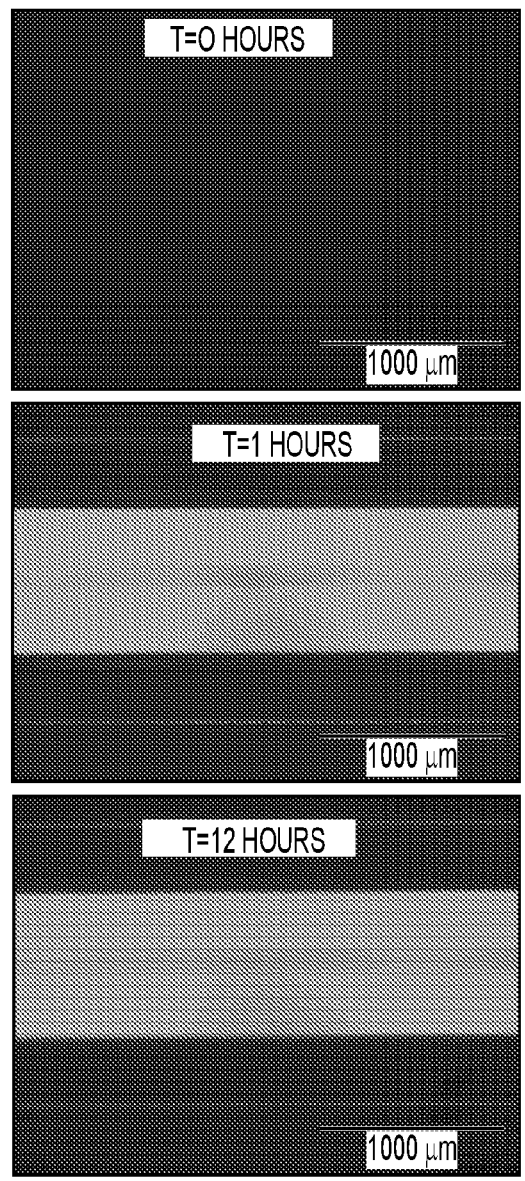

A singular microfluidic unit within Mimetas 2-lane ORGANOPLATE® is shown (Well 1 to Well 4) (FIG. 1A). A standard 384 well plate contains 96 repeats of the 2-lane microfluidic system. The microfluidic channels of 9603-400B Mimetas 2-lane ORGANOPLATES® were completely filled with 4 mg/ml collagen (pre-gel volumes added: well 1: 2.5 µl and well 4: 2.5 µl) to create an end-to-end collagen extracellular matrix (ECM) plug. Adding excess of 5 µl of pre-gel into well 1 did not fill the entirety of the channel contents with the ECM gel (FIG. 1B). Addition of 2 mg/ml 10 kDa FITC-Dextran (2 µM) in 1×PBS in well 4 resulted in immediate movement of the FITC-Dextran as detected by increase in the fluorescent signal in the observation channel (well 3) (high hydrostatic pressure differential setting) (ex: 488 nm, em: 530 nm) at 1 hour and 12 hours (FIGS. 1C-D).

Figure 1D:
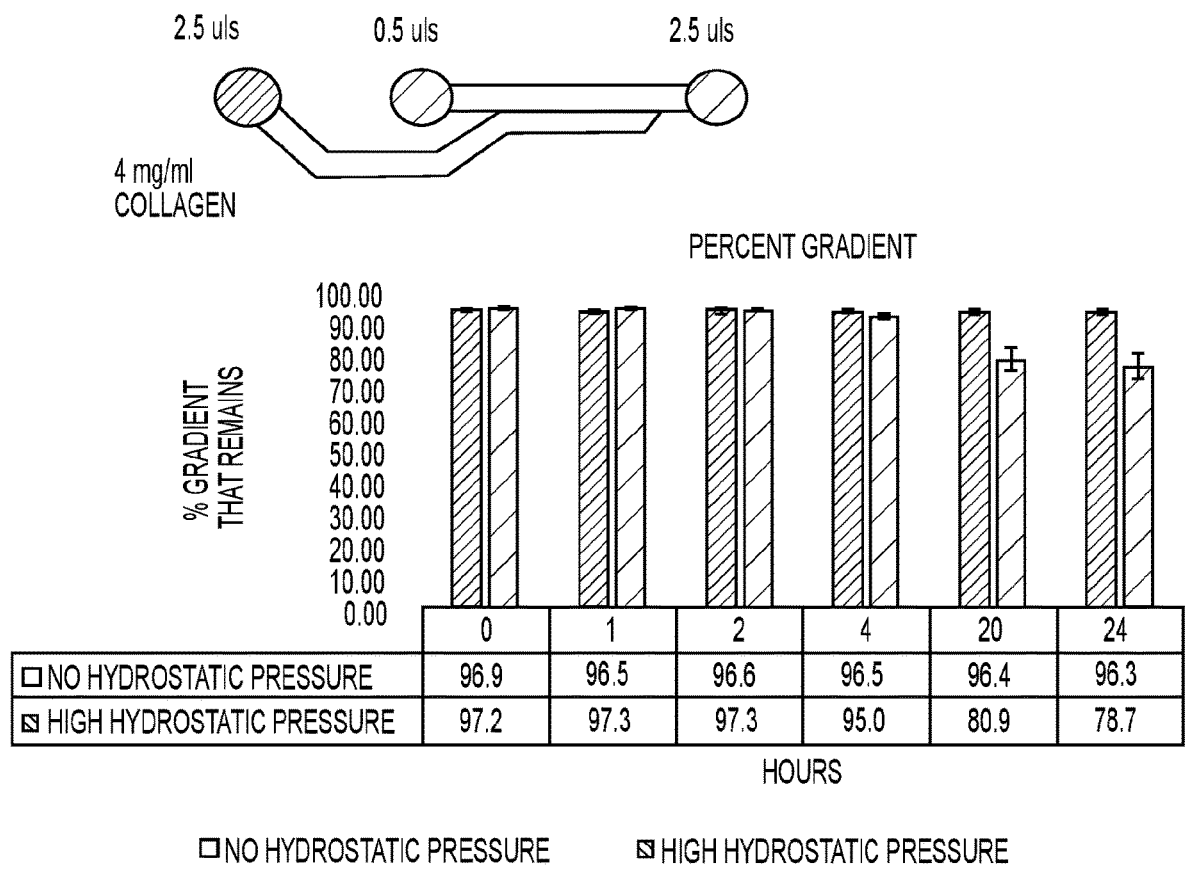

Estimation of the gradient generated with placement of different volumes of 1 µM 10 kDa FITC-Dextran into well 4 indicated initial similarities in the gradient (up to 4 hours) followed by a prominent divergence (well 1: 2.5 µl, well 4: 2.5 µl, well 2: 0.5 µl of 4 mg/ml collagen) (FIG. 1D). Almost 96% of gradient remained in the "no hydrostatic pressure differential" setting vs only 78% in the "high hydrostatic pressure differential" setting after 24 hours of the diffusion experiment (FIG. 1D). These results indicated that higher diffusion gradient could be established for a longer timeframe without hydrostatic pressure differential (FIG. 1D). Addition of 0.5 µl of 4 mg/ml collagen into well 2 allowed significantly higher migration of T-cells compared to 0 µl 4 mg/ml collagen of ECM added (data not shown).

EXAMPLE 4

Assay Set Up Improvements within 2-Lane Mimetas ORGANOPLATE® to Facilitate Robust Chemotaxis The assay was further improved with incorporation of matrigel GFR into the collagen ECM to create a blend of 2 mg/ml collagen mixed with 10% (v/v) matrigel GFR to improve the ECM protein diversity within the solid matrix. In order to create aligned collagen fibers in the direction of the generated gradient within the microfluidic channel of 9605-400B Mimetas 2-lane ORGANOPLATE® to facilitate migrating cells, we added larger amount of the pre-gel ECM to well 4 (5 µl) followed by 1 µl of pre-gel into wells 1 and 2 in two distinct stages. Stage by stage addition of the pre-gel allowed complete filling of the microfluidic channel before addition of pre-gels into wells 1 and 2 to create a seamless ECM plug with ECM footprints in all the wells (FIG. 2a). A bright field imaging of the contents of well 4 showed aligned collagen fibers after the following addition as described above (FIG. 2A (lower left)).

In order to estimate a robust set-up towards activated T-cell chemotaxis within the end-to-end ECM filled 2 lane Mimetas ORGANOPLATE®, three different assay arrangements of the chemotaxis stimuli and activated CD3+ T-cells were considered (FIG. 2B). T-cells were added closer to the mouth of the channel in all conditions (or assay arrangements) to provide them with highest dose of the chemokine stimuli available for migration. Our results showed that adding activated CD3+ T-cells closer to the mouth of the channel in well 2, with media in well 1 and chemokine in well 4 resulted in significantly higher chemotaxis with 300 nM CXCL12 compared to 0 nM CXCL12 (at 120 hours) (FIG. 2B). The chemokine was refreshed after 48 hours during the assay.

Minimal chemotaxis response was observed in 48 hours with the recombinant chemokines in comparison to longer timeframes of 96 and 120 hours (data shown in supporting information, FIG. S2). Significantly higher number of activated CD3+ T-cells were noted to respond to the chemotaxis stimuli in assay arrangement 1 in comparison to arrangements 2 and 3 (300 nM vs 0 nM) (FIG. 2B). Based on the results of our assay development experiments, we created the final version of the assay, consisting of ECM footprint in all wells, connected with aligned collagen fibers mixed with 10% matrigel GFR (ECM plug) in the central channel, with the migrating stimuli added in well/frame 4 which was refreshed after 48 h. Activated CD3+ T-cells were added closer to the mouth of the channel in well/frame 2, and blank media in well/frame 1 (FIG. 2C). A chemokine gradient from the higher concentration of the chemokine (well/frame 4) to the lower concentration (well/frame 2) triggers responding migratory cell movement against the gradient (arrow) (FIG. 2C). Positioning of well 2 with the cells of interest in between wells 1 and 4 causes the chemokine gradient to push deeper into the well resulting eliciting a pro- or anti-chemotaxis response from the desired cell (placed close to the mouth of the channel). This arrangement was designed specifically to study activated CD3+ T-cell chemotaxis towards different chemotactic stimuli.

EXAMPLE 5

Activated CD3+ T-Cell Chemotaxis Through End-to-End Collagen-Matrigel ECM Plug within 2-Lane Mimetas ORGANOPLATE® in Response to CXCR3 Agonist, Recombinant CXCL10 and CXCL12

Figure 3A:
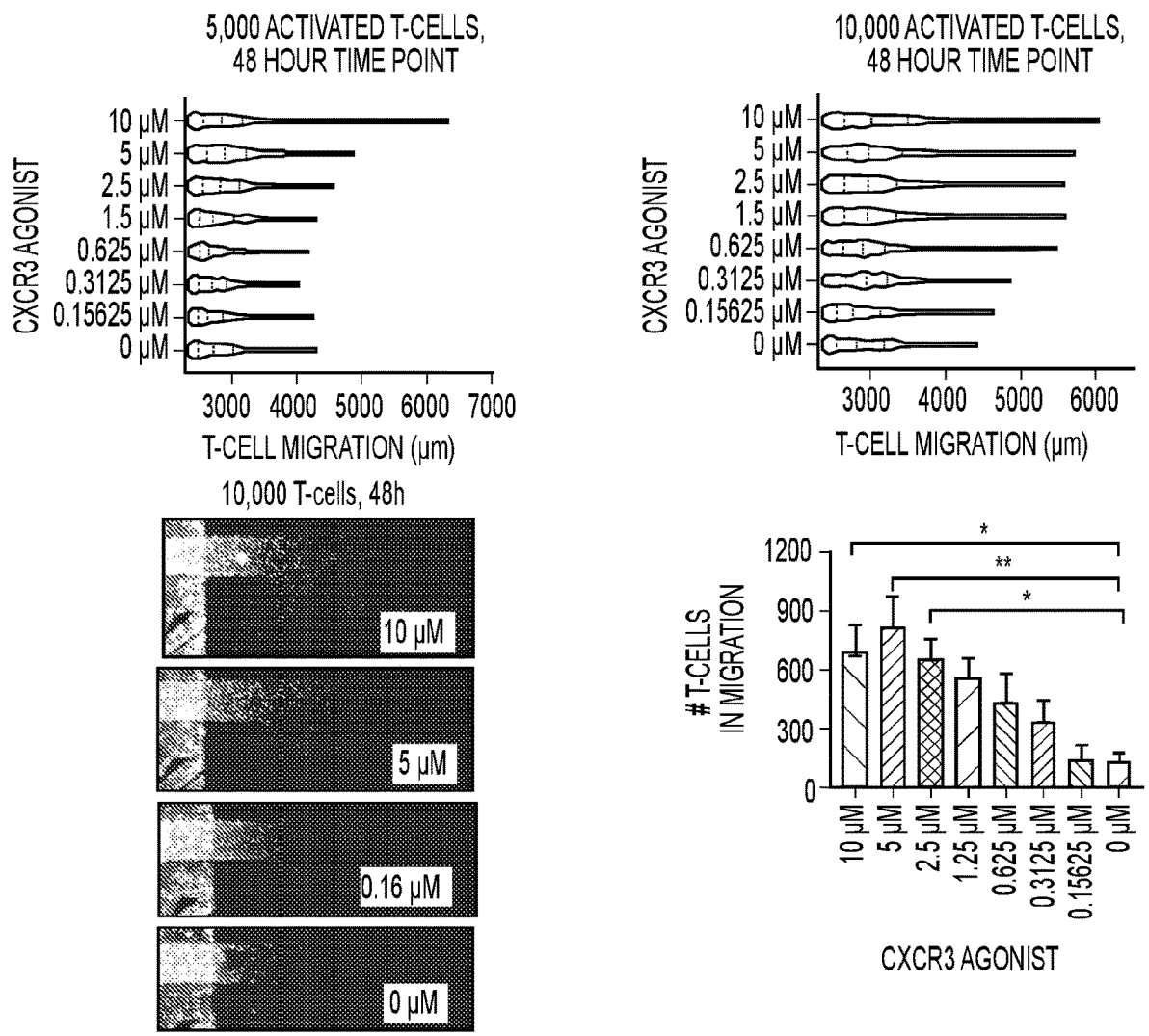
FIG. 3A-3C.

Different concentrations of small molecule CXCR3 agonist were applied to one end of the ECM plug (well/frame 4) and different activated CD3+ T-cell numbers were added closer to the mouth of the channel at the other end (well/frame 2) to evaluate chemotaxis in response to the small molecule agonist. We observed a robust response by the activated CD3+ T-cells as noted by their rapid movement into the ECM plug in response to the small molecule agonist gradient. At 5000 cells, only 10 µM and 5 µM concentration of CXCR3 agonist showed a higher activated T-cell chemotaxis response compared to 0 µM in 48 hours (average sample median numerically greater than blank). However, at 10,000 cells, we observed that all the concentrations from 10 µM to 0.3 µM of CXCR3 agonist showed a higher T-cell chemotaxis response in comparison to 0 µM blank media control (average sample median numerically greater than blank) (FIG. 3A). Due to the very robust response of the T-cells to the CXCR3 small molecule agonist, the experiment was ended within 48 hours. We also measured the total number of T-cells that responded to the chemokine gradient by counting the total number of T-cells in the response channel. Significantly higher number of activated T-cells (5-6 fold higher) were observed to migrate into the channel in response to CXCR3 agonist gradient at concentrations of 10 µM, 5 µM, and 2.5 µM compared to blank media control within 48 hours (FIG. 3A) (One-way ANOVA test).

Figure 3B:
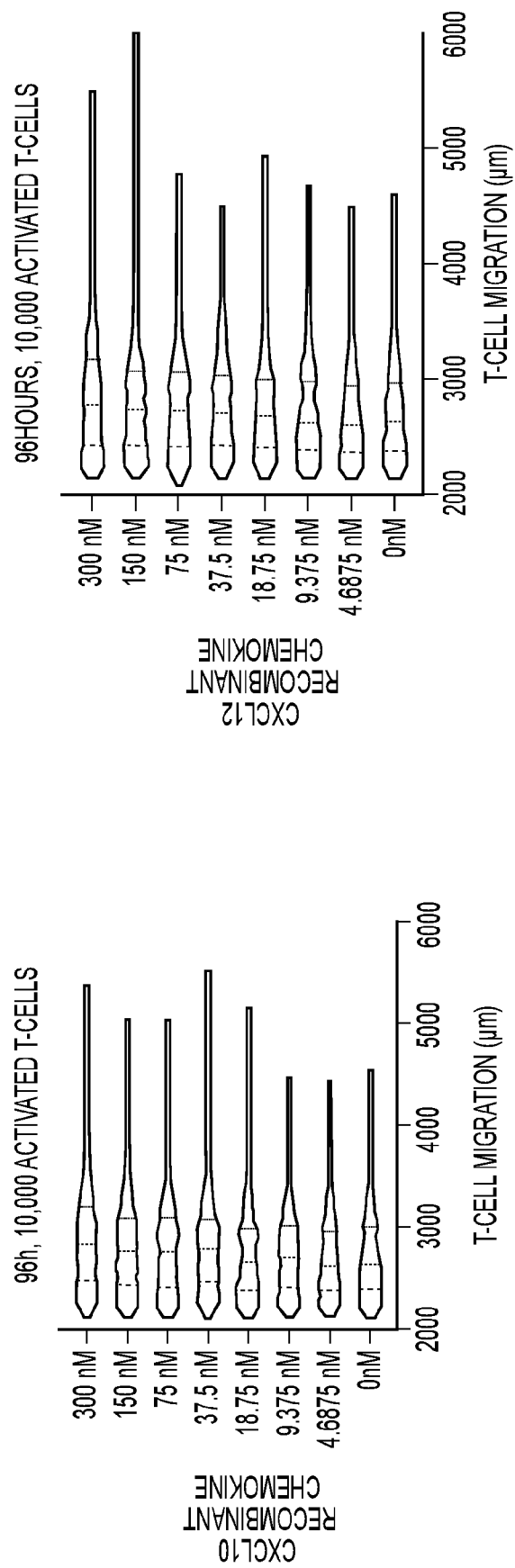
Figure 3C:
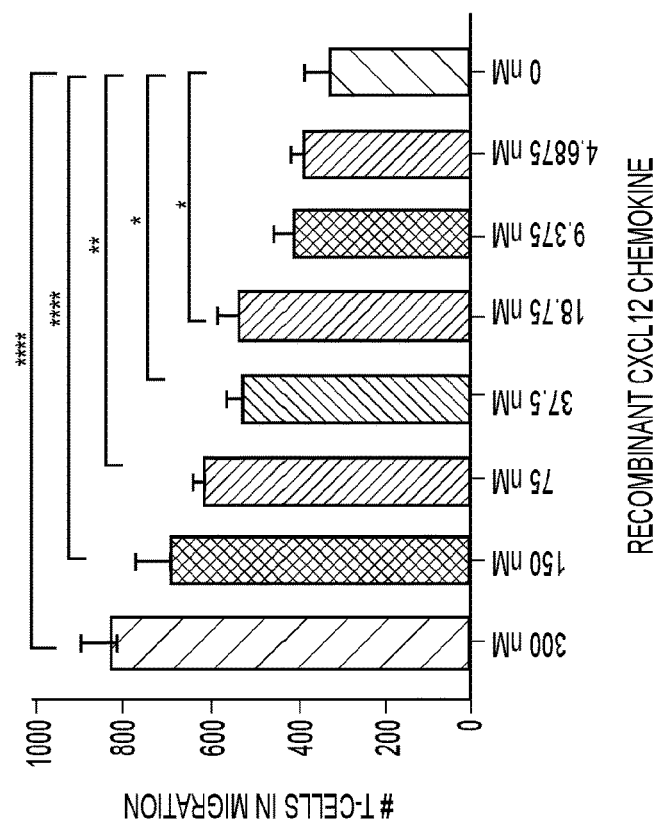
Figure 3C:
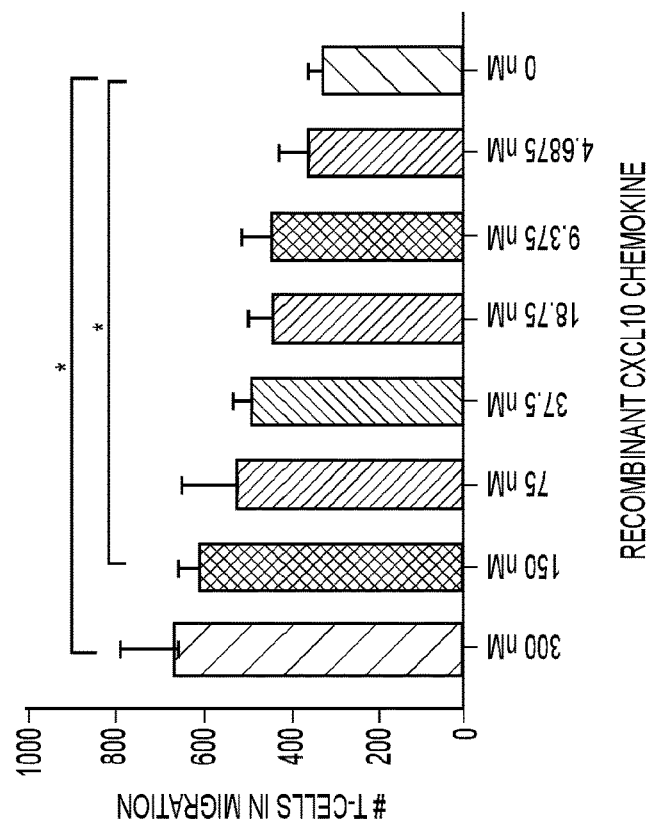

We also studied the response of activated CD3+ T-cells against recombinant chemokines CXCL10 and CXCL12 in the end-to-end collagen-matrigel ECM plug within 2-lane Mimetas ORGANOPLATE®. As we previously observed minimal chemotaxis response in 48 hours with the recombinant chemokines, we recorded the response window at 96 and 120 hours. Chemokine concentrations were also refreshed at 48-hour time point. At 10,000 cells, we observed a robust chemotaxis response with both the CXCL10 and CXCL12 recombinant chemokines at 96 hours. With both CXCL10 and CXCL12 recombinant chemokines, we observed a robust chemotaxis response up to 37.5 nM when compared to blank media control (0 nM) (average sample median numerically greater than blank) (FIG. 3B). With regard to the total number of activated T-cells that responded to the chemokine gradient, in CXCL12 recombinant chemokine a significantly higher chemotaxis response extended to 18.75 nM over blank media controls, whereas only 150 nM was significantly higher than blank media controls for CXCL10 chemokine (FIG. 3C) (One-way ANOVA test). These results indicate the effectiveness of this model system to understand chemotaxis via multiple metrics (distance migrated and number of migratory T-cells), which is difficult to do with traditional TRANSWELL™ assays.

Activated CD3+ T-cells responded strongly to different chemokines such as CXCR3 agonist, CXCL12, and CXCL10 in a concentration dependent manner. Activated CD3+ T-cells showed a robust chemotaxis response against small molecule CXCR3 agonist within the first 48 hours compared to recombinant chemokines CXCL10 and CXCL12, likely due to the faster diffusion of the small molecule in comparison to the larger recombinant chemokines. Chemotaxis was observed and quantified via multiple metrics, such as the maximum distance travelled and the total number of responsive T-cells.

EXAMPLE 6

Figure 6A:
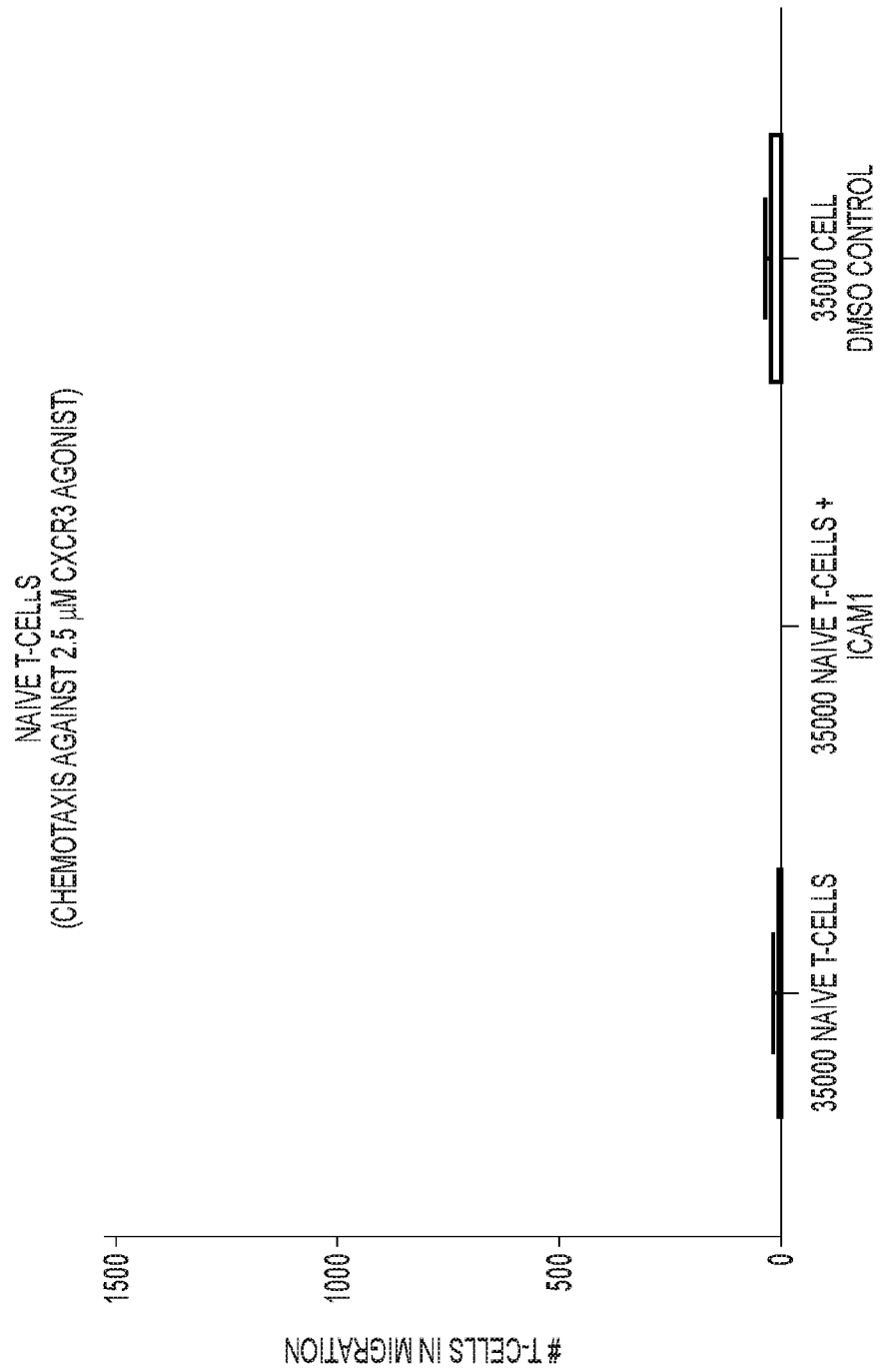
FIG. 6: Nuclight rapid red dye stained naive CD3+ T-cells were added closer to the mouth of the channel at the one end (well/frame 2 (102)) of extracellular matrix (2 mg/mL collagen+10% (v/v) Matrigel GFR) filled within 2-lane Mimetas ORGANOPLATE®) to evaluate chemotaxis in response to the small molecule agonist applied to other end of the extracellular matrix plug (well/frame 4 (104)). Well/frame 1 (101) was filled with blank media. Chemotaxis potential was measured via confocal microscopy, identifying the number of naïve T-cells under migration in response to the chemokine gradient generated within the extracellular matrix.
As shown in FIG. 6B, all of the higher cell numbers tested (100,000; 125,000 and 150,000 cells) demonstrated significant chemotaxis against 2.5 µM of CXCR3 agonist in comparison to DMSO control. Statistical significance of the T-cell migration cell counts are shown with , *, and **** in FIG. 6B.
Figure 6B:
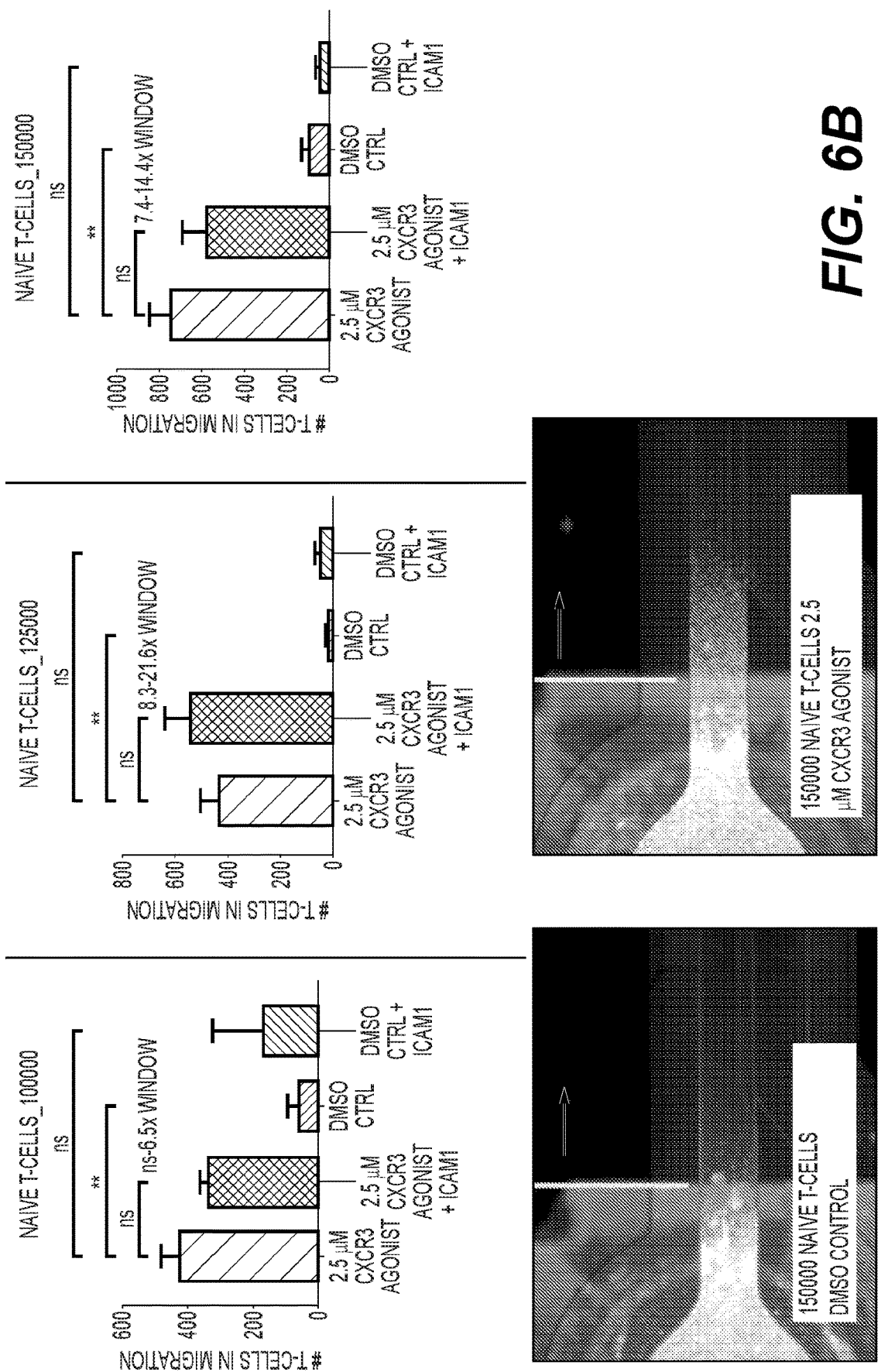

Naive CD3+ T-Cell Chemotaxis Through End-to-End Collagen-Matrigel Extracellular Matrix Plug within 2-Lane Mimetas ORGANOPLATE® in Response to CXCR3 Agonist Nuclight rapid red dye stained naive CD3+ T-cells were added closer to the mouth of the channel at the one end (well/frame 2 (102) of extracellular matrix (2 mg/mL collagen+10% (v/v) Matrigel GFR) filled within 2-lane Mimetas ORGANOPLATE®) to evaluate chemotaxis in response to the small molecule agonist applied to other end of the extracellular matrix plug (well/frame 4 (104)). Well/frame 1 (101) was filled with blank media. Unlike activated CD3+ T-cells, the naïve CD3+ T-cells do not experience Trans-Act™ driven proliferative burst after their addition to the chip (well/frame 2). Further, naïve CD3+ T-cells also have a significantly lower expression of the CXCR3 receptor (data not shown). Hence, higher cell numbers of the naïve T-cells were added to investigate chemotaxis against 2.5 µM of CXCR3 agonist. In order to enhance the adhesion of naïve T-cells to the extracellular matrix, 1 µg/mL of ICAM1 (Intercellular Adhesion Molecule 1, also known as Cluster of Differentiation 54 (CD54)) was also spiked into well/frame 2 of the assay system along with the T-cells. Chemotaxis potential was measured via confocal microscopy, identifying the number of naïve T-cells under migration in response to the chemokine gradient generated within the extracellular matrix. Our observations indicated a minimal detectable chemotaxis at 35000 Naïve T-cells added to well/frame 2 against 2.5 µM of CXCR3 agonist (FIG. 6A). Addition of ICAM1 did not influence the number of naïve T-cells that responded to the chemokine gradient (FIG. 6A). Increasing the number of naïve T-cells added to the well/frame 2 significantly improved the chemotaxis results (FIG. 6B). As shown in FIG. 6B, all of the higher cell numbers tested (100,000; 125,000 and 150,000 cells) demonstrated significant chemotaxis against 2.5 µM of CXCR3 agonist in comparison to DMSO control. Inclusion of ICAM1 into well/frame 2 along with the higher number of naïve T-cells also had a non-significant impact on the chemotaxis outcome, similar to the results obtained at lower cell numbers (35000 cells, FIG. 6A). At the higher naïve T-cell numbers, a window of (ns-6.5×) for 100,000 cells; (8.3-21.6×) for 125,000 cells and (7.4-14.4×) for 150,000 over DMSO control (with or without ICAM1) was observed (FIG. 6B). The insert in FIG. 6B shows the day 4 chemotaxis data of 150,000 naïve T-cells responding to either DMSO (dimethyl sulfoxide) control or 2.5 µM CXCR3 agonist gradient generated within the extracellular matrix filled 2-lane Mimetas ORGANOPLATE® (the white line indicates the region beyond which the T-cell numbers are counted for analysis). These results indicate the versatility of the extracellular matrix filled 2-lane Mimetas ORGANOPLATE® platform in demonstrating chemotaxis with different immune cells responding to varied chemotaxis stimuli gradients.

EXAMPLE 7

Variability of Extracellular Matrix Filled 2-Lane Mimetas ORGANOPLATE® Across the 384-Well Plate In order to identify the variability of the crosslinked extracellular matrix across the 384 well plate, 50 µLs of 10 µM FITC dextran (10 KDa) (fluorescein isothiocyanate linked to dextran where the dextran had an average molecular weight of 10 KDa) in 1×PBS (phosphate buffered saline) was added into well/frame 4 (104) of 48 wells of the extracellular matrix filled 2-lane Mimetas ORGANOPLATE®. After 24 hours, the 40 µLs of the contents from well/frame 2 were collected for fluorescence quantification. A blank PBS was used as a control.

Figure 7:
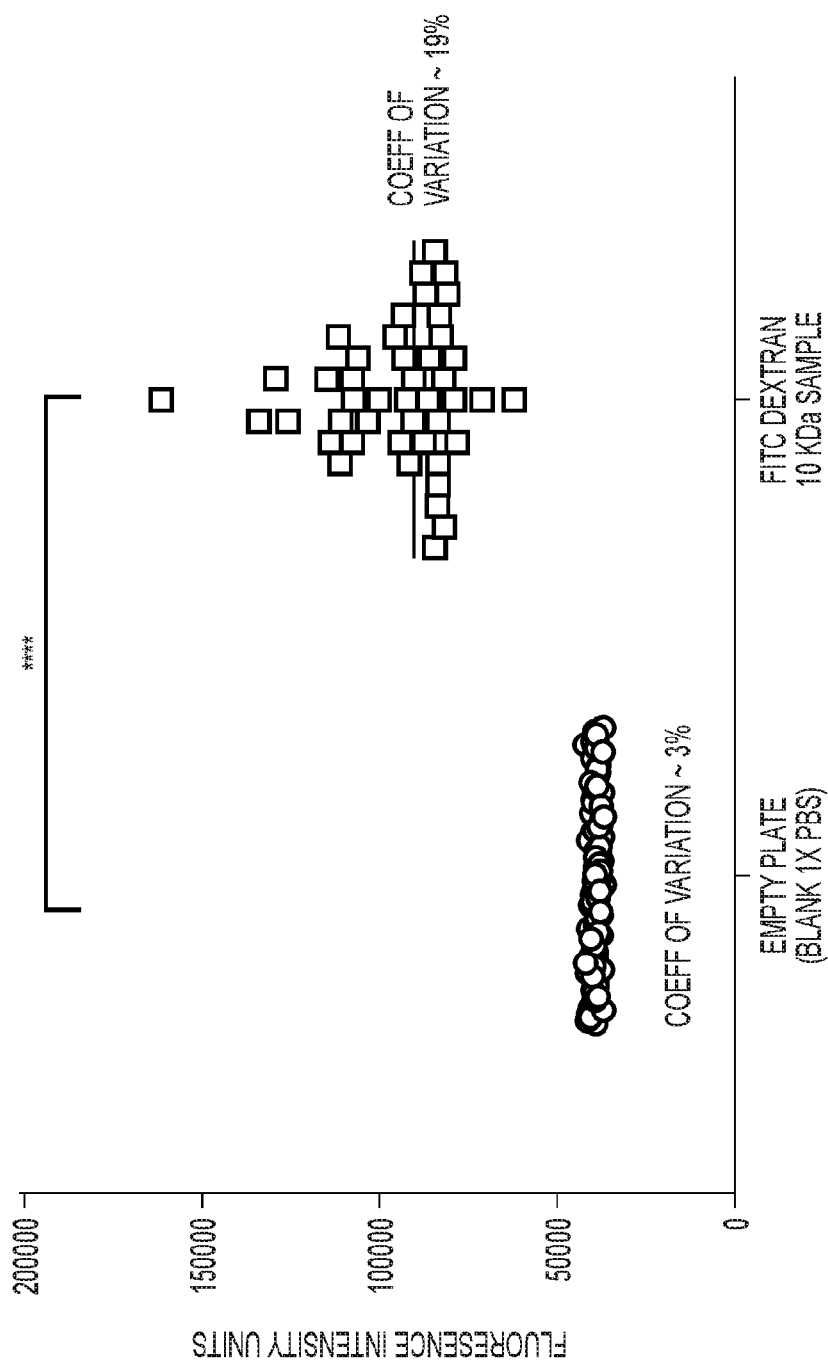
FIG. 7: Demonstrates the variability of the crosslinked extracellular matrix across the plate: the matrix varies by approximately 16%.

As shown in FIG. 7, the crosslinked extracellular matrix varied approximately 16% across the plate and demonstrated performance of automated extracellular matrix dispensing and crosslinking across the plate and provided a suitable substrate.

EXAMPLE 8

Fluidic Focusing of a Chemokine Mimic within the Extracellular Matrix Filled 2-Lane Mimetas ORGANOPLATE® Via Intentional Creation of a Hydrostatic Pressure Differential Method of extracellular matrix dispensing into the wells of 2-lane Mimetas ORGANOPLATE® (FIG. 2) creates their strong presence and footprint in each of the 4-well Mimetas ORGANOPLATE® unit (96 units per plate). Media addition atop the ECM after their crosslinking also connects the wells fluidically with each other through the ECM spaces. We observed that rapid delivery of chemokine/solute of interest into well/frame 2 (102) could be facilitated by selectively removing the liquid contents from well 2 (102) (after 24 hours of addition), thereby creating a hydrostatic pressure differential between the wells. Due to the fluidically linked nature of the wells, we observed an interesting pattern of content movement within the wells (FIG. 8).

Figure 8A:
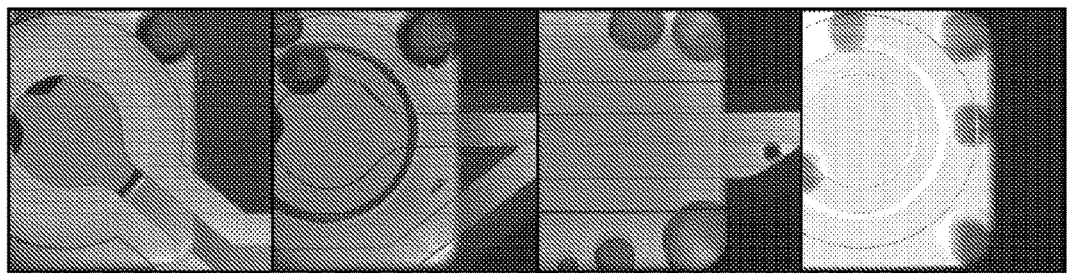
FIG. 8: Demonstrates the ability to produce differential hydrostatic pressure to drive fluidic focusing of a chemokine, or other agent, within the extracellular matrix filled 2-lane Mimetas ORGANOPLATE®.
Figure 8B:
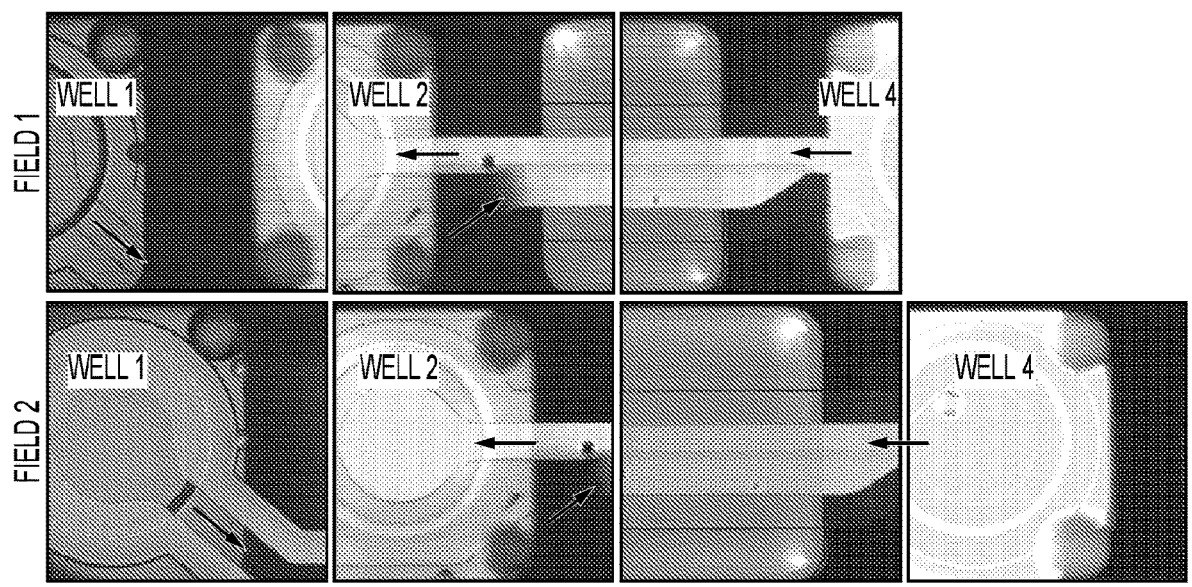
Figure 8C:
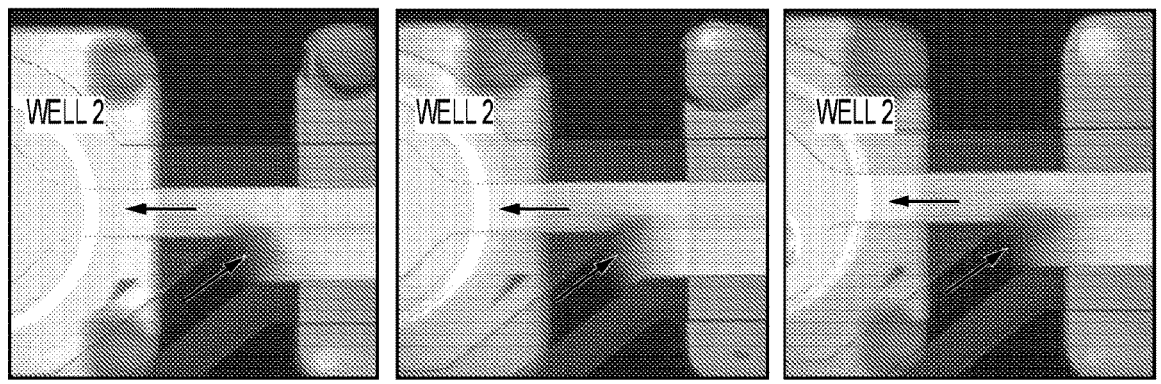
Figure 8D:
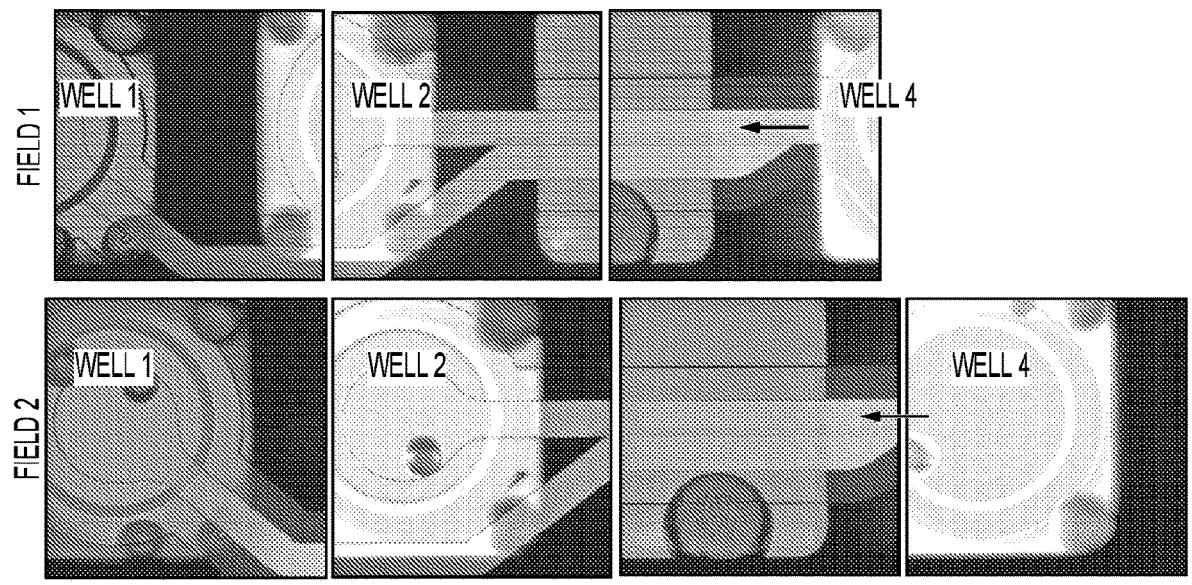
Figure 8E:
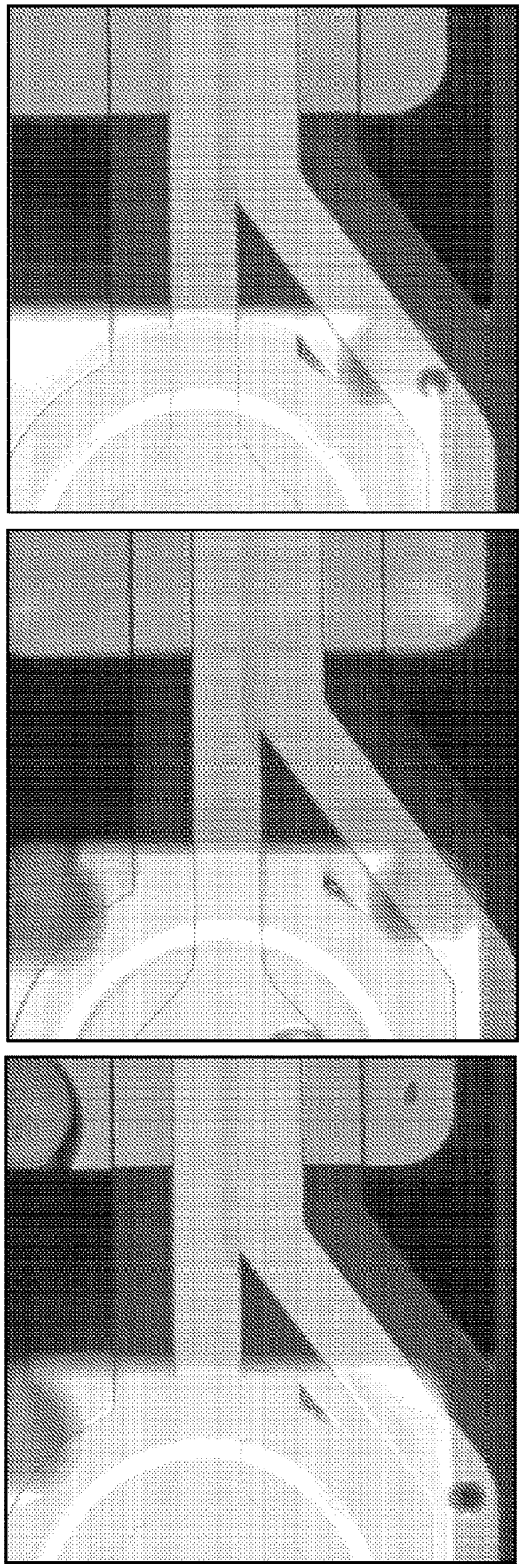

50 µLs of 10 µM FITC dextran (10 KDa) in 1×PBS was added into well/frame 4 (104) of the extracellular matrix filled 2-lane Mimetas ORGANOPLATE® whereas wells/frames 1 (101) and 2 (102) received 50 µLs blank 1×PBS. 24 hours after the initiation of diffusion, selective intentional removal of 40 µLs of well 2 contents created a hydrostatic pressure differential allowing fluid movement and pressure readjustment in the 4 well connected system. As shown in FIG. 8A-C, removal of liquid content from well/frame 2 caused fluidic flow from connected wells/frames 1 and 4 allowing a focusing of the FITC dextran into well 2 in response. Movement of blank media from well 1 towards well 2 enhanced FITC dextran movement from well 4 towards well 2 (demonstrated in white and black arrows). Longer length of ECM (extracellular matrix) from wells 1 to 2 in comparison to wells 4 to 2 allowed the fluidic focusing of well 4 contents into well 2 (FIG. 8A-C). Diffusion of the FITC dextran towards well 1 proceeded subsequent to the readjustment (day 6 image) (FIG. 8D-E). These results demonstrate the ability to specifically produce a desired fluidic focusing of a chemokine mimic within the extracellular matrix filled 2-lane Mimetas ORGANOPLATE® through intentional creation of a hydrostatic pressure difference between the connected wells (differential pressure).

EXAMPLE 9

Optimization of HT29-GFP Colorectal Cancer Culture and Killing within End-to-End Collagen-Matrigel Extracellular Matrix Plug within 2-Lane Mimetas ORGANOPLATE® Towards CART Cell Chemotaxis and Killing (Chemotaxis and Function)

Figure 9A:
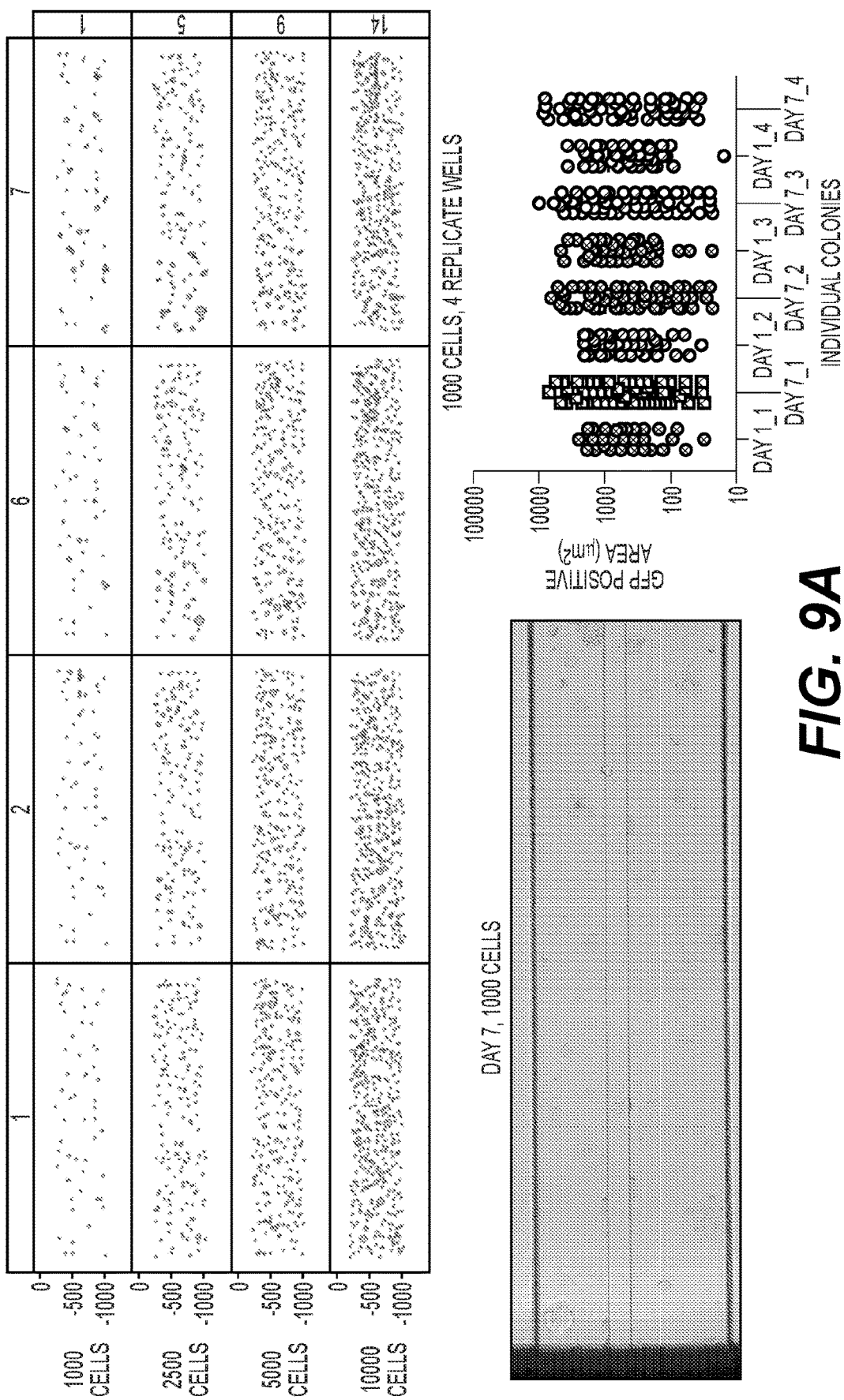
FIG. 9: Shows cell culture of HT29-GFP colorectal cancer cells (in single cell colonies and spheroid clusters) within the extracellular matrix filled microfluidic channel.
FIG. 9D shows cancer cell killing by bortezomib treatment and the cell killing detected by identifying GFP cell debris.

To demonstrate chemotaxis and function via this 2-lane assay, we incorporated cancer cell single cell colonies and spheroid clusters within the extracellular matrix filled within the microfluidic channel. Single cell suspension of (1000, 2500, 5000 and 10,000) HT29-GFP colorectal cancer cells double filtered with 20 µm filter were mixed in the collagen-matrigel pregel and dispensed into well/frame 4 (104) of the 2-lane Mimetas ORGANOPLATE® and were observed for cell growth for up to 7 days (FIG. 9A). Single cells were seen to be uniformly dispensed across the microfluidic lanes and grew into single cell colonies over time. Cells closest to the base of the microfluidic lanes settled down and showed monolayer like growth (FIG. 9A).

Figure 9B:
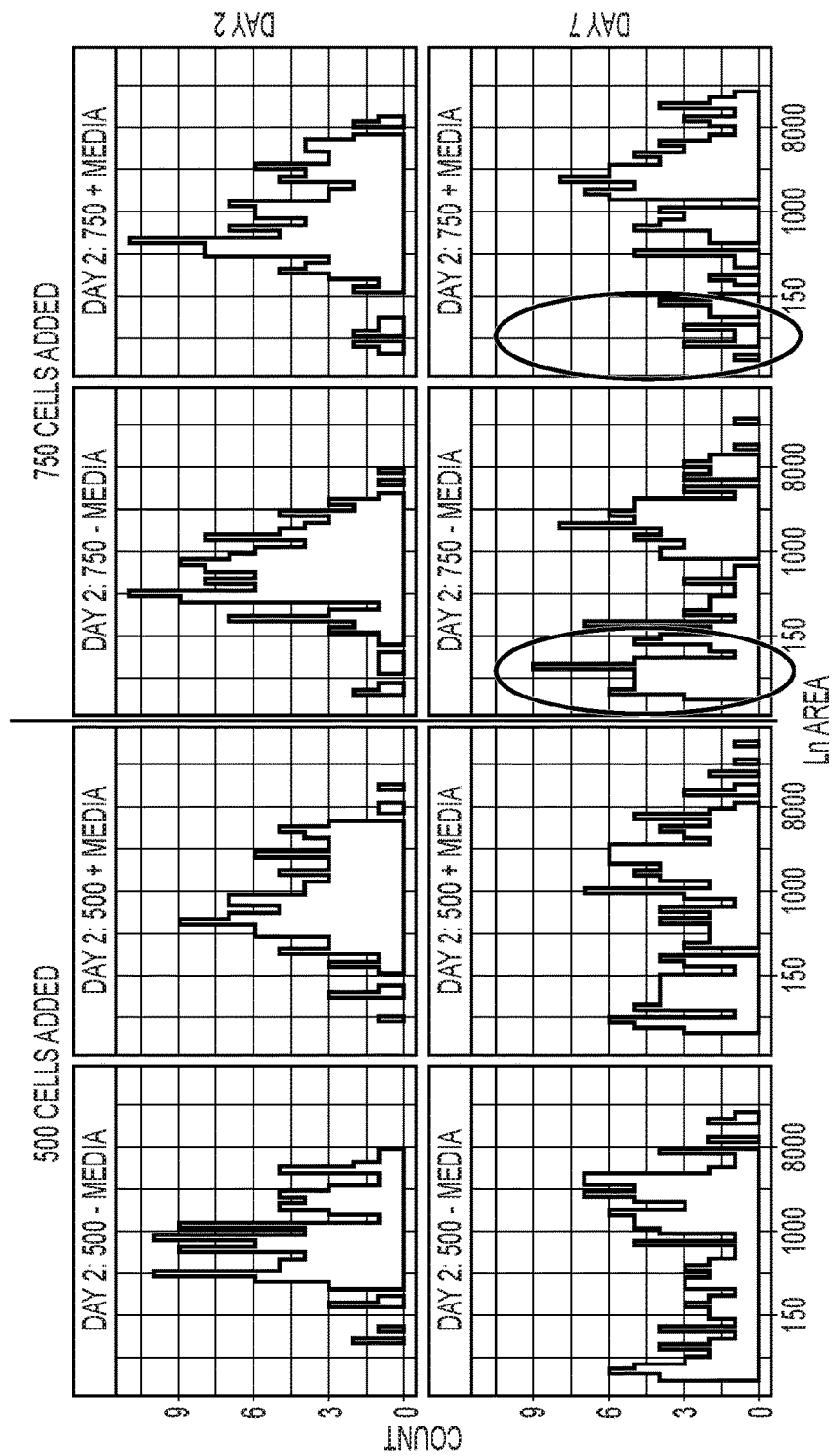

The higher throughput of the 2-lane Mimetas ORGANOPLATE® also allowed optimization of cell growth protocols of cells grown within the microfluidic channels. As shown in FIG. 9B, absence of cell growth media added into the well/frame 2 (102) of the 4-well unit likely influences the growth of single cell colonies closer to the well/frame 2 at higher cell numbers.

Figure 9C:
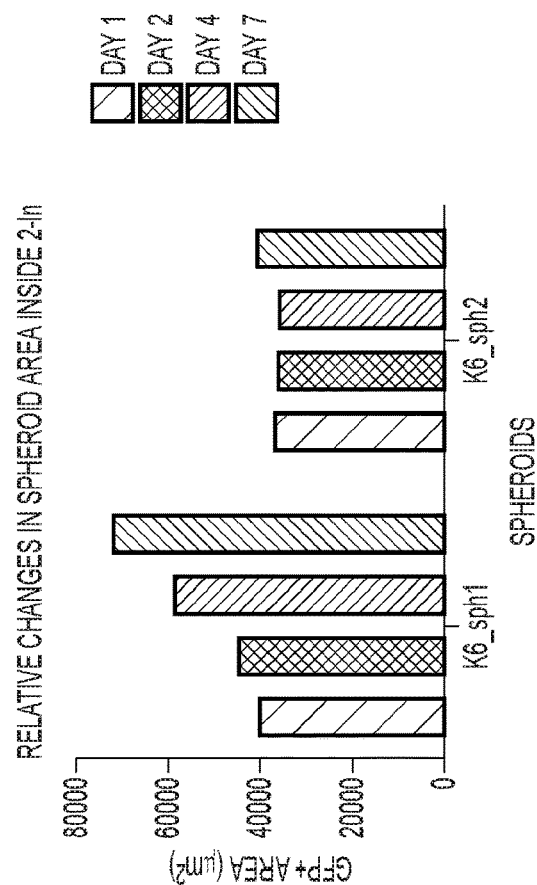
Figure 9C:
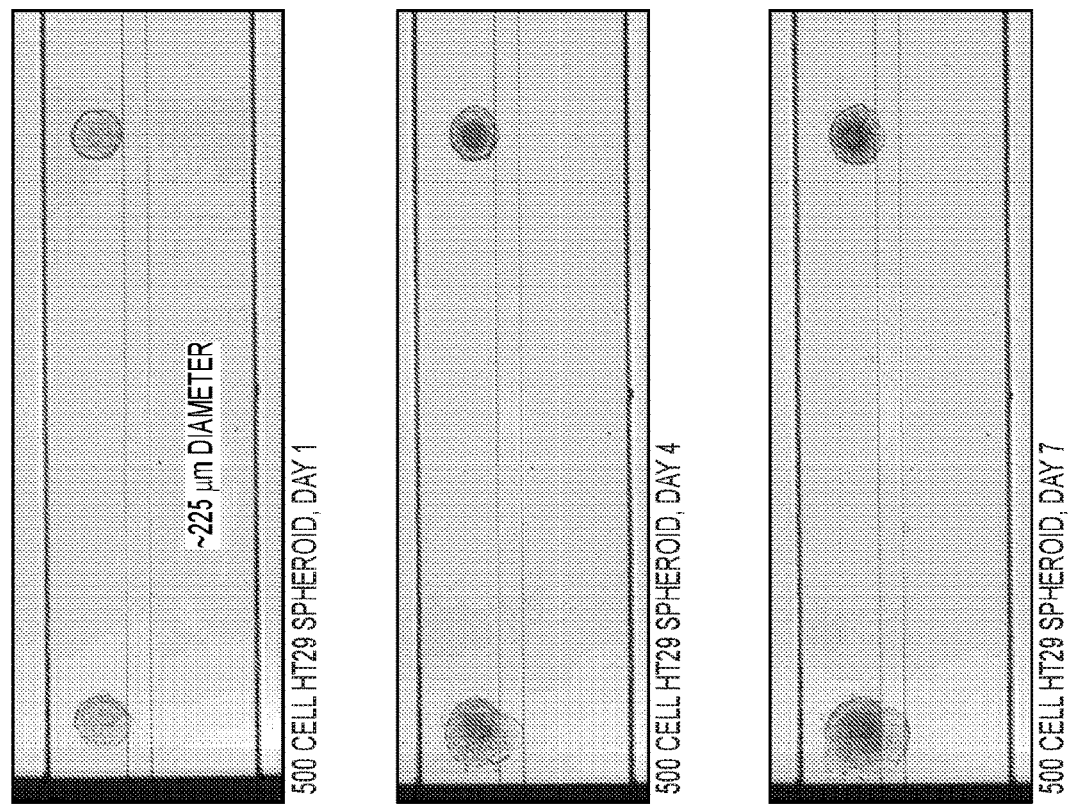

In another embodiment, 2-day old 500 cell spheroids generated within ultralow attachment plates were mixed into the pregel and dispensed into well/frame 4 of the 2-lane Mimetas ORGANOPLATE® and were observed for cell growth for up to 7 days (FIG. 9C).

Figure 9D:
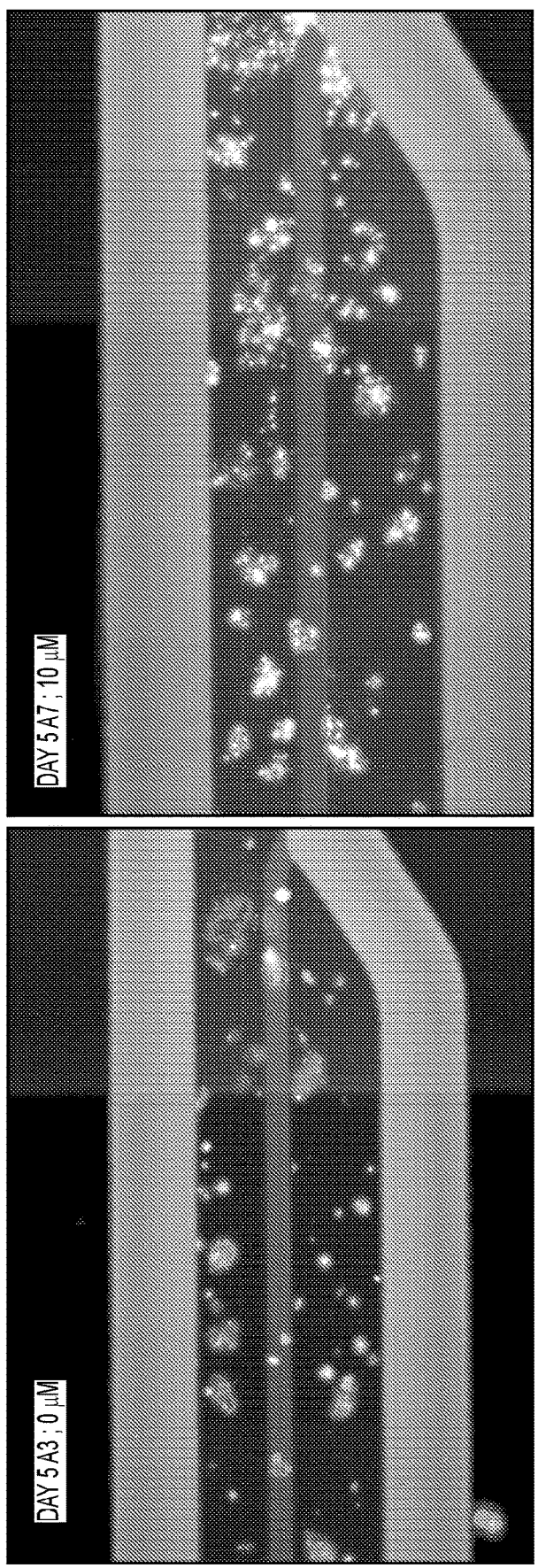
Figure 9D:
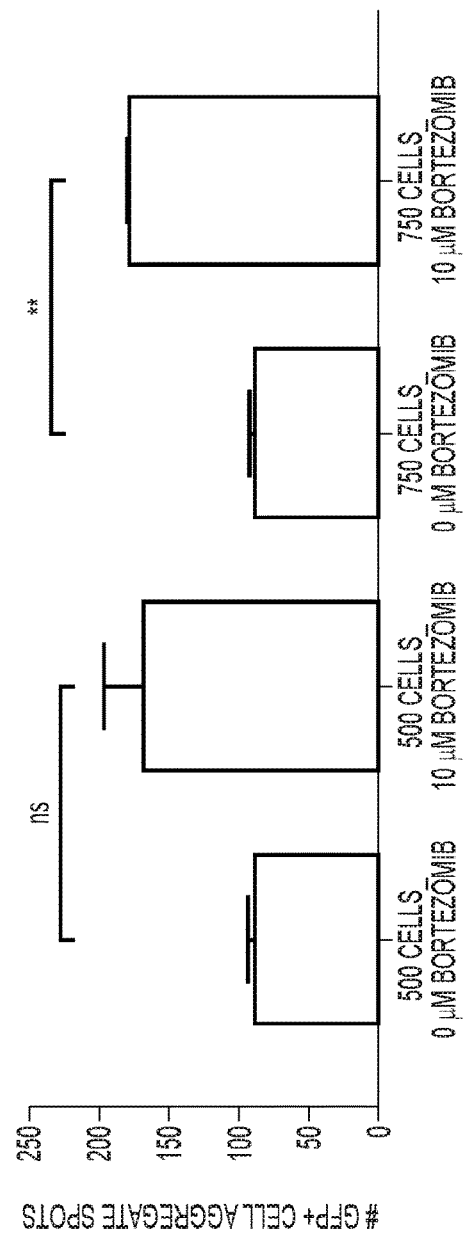

2-lane Mimetas ORGANOPLATE® wells harboring 7-day old single cell colonies with either 500 cells or 750 cells were treated with 0 or 10 µM Bortezomib (sold under the brand name Velcade in the United States; CAS 179324-69-7) to observe cell killing within the channel over 5 days. As shown in FIG. 9D, Bortezomib treatment resulted in higher intensity, punctate GFP cell debris aggregates and image analysis algorithm designed specifically to capture those debris detected a statistically significant increase in the number of the cell aggregates in the bortezomib treated wells (750 cells).

These results indicate that extracellular matrix filled 2-lane Mimetas ORGANOPLATE® can harbor different attributes of tissue microenvironment as either single cells/cancer cells or spheroidal cell clusters (tumor spheroids) which respond to chemotherapeutic drug treatment as detected by the changes in the cell surface area (via confocal microscopy). These cells filled extracellular matrix constructs can be further used to demonstrate immune cell chemotaxis and function in tissue relevant 3D spaces with detectable outcomes.

EXAMPLE 10

Demonstrating CART Cell Driven Cancer Cell Killing within End-to-End Collagen-Matrigel Extracellular Matrix Plug in 2-Lane Mimetas ORGANOPLATE®

Figure 10A:
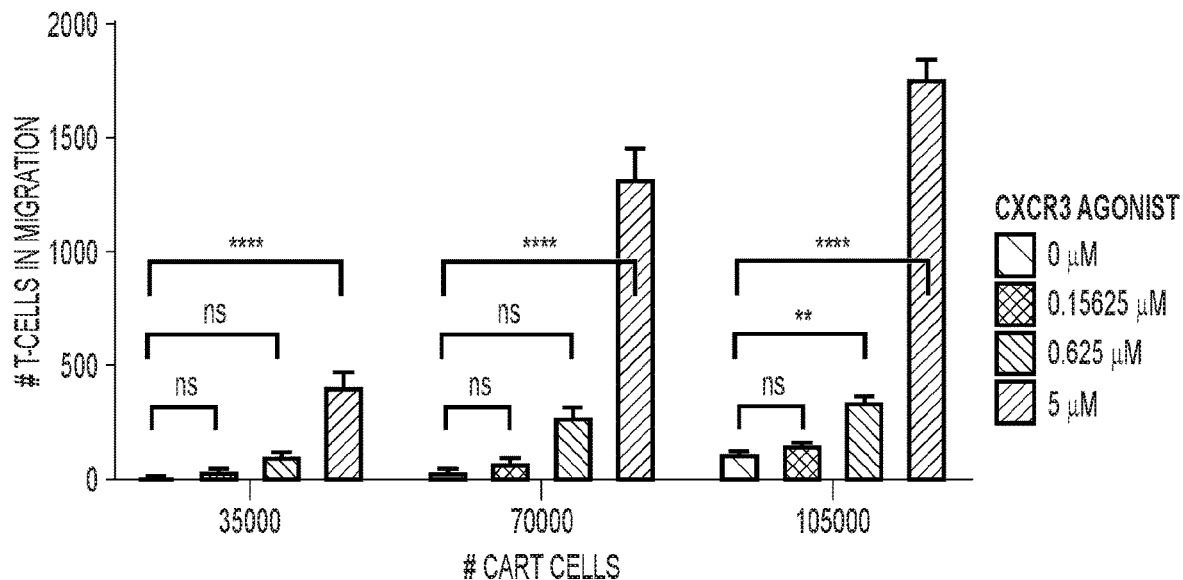
FIG. 10: Shows chemotaxis and kill responses by CD4/CD8 CART cells in response to CXCR3 agonists.
Figure 10B:
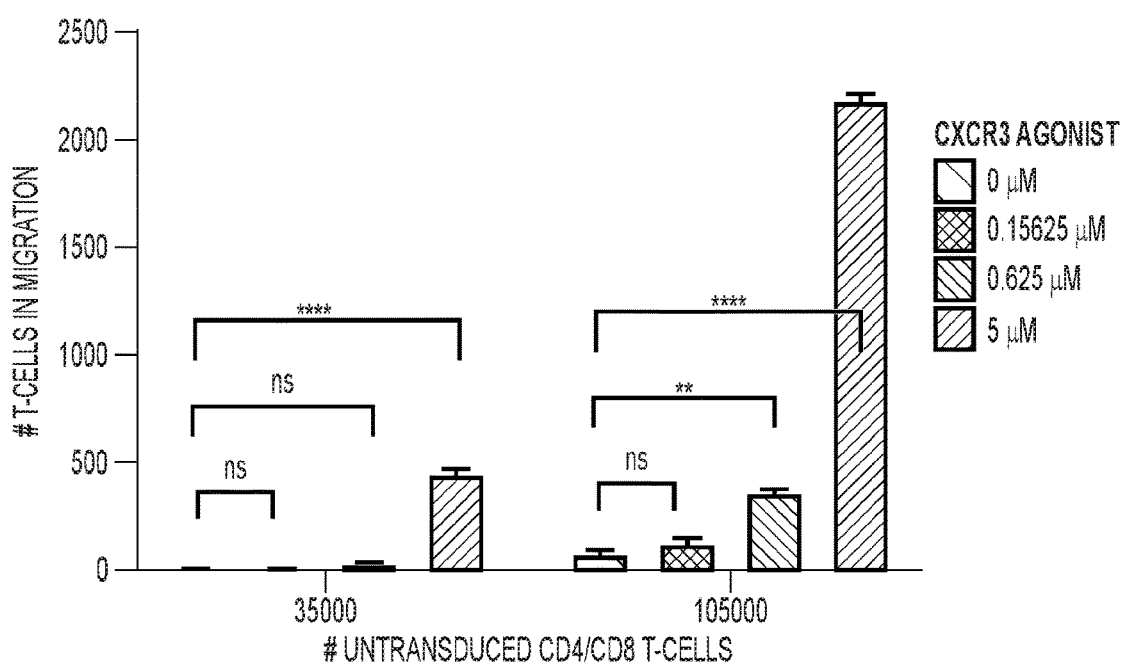
Figure 10C:
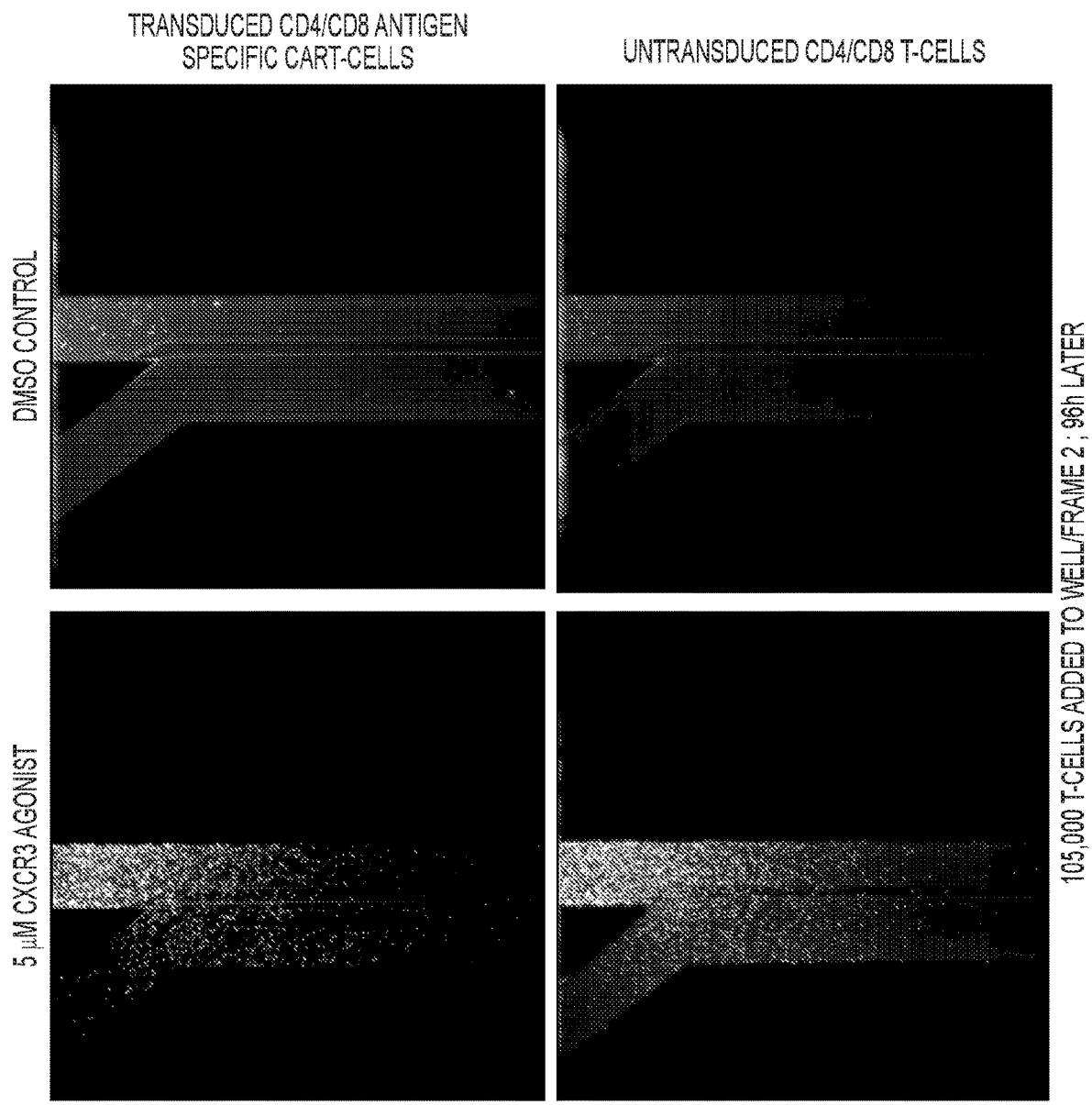

In order to demonstrate chemotaxis and function within the 2-lane Mimetas ORGANOPLATE®, we firstly studied antigen specific CD4/CD8 CART-cell (CD4/CD8 Chimeric Antigen Receptor T-cell) chemotaxis against CXCR3 agonists within the plate. NucLight® rapid red dye (Incucyte) stained 35,000, 70,000 and 105,000 transduced CD4/CD8 antigen specific CART-cells and untransduced CD4/CD8 T-cells were added to well/frame 2 (102) of 4-well 2-lane Mimetas ORGANOPLATE® units filled with 2 mg/ml collagen+10% (v/v) matrigel GFR exposed to a CXCR3 agonist gradient. As shown in FIG. 10A, both transduced CD4/CD8 antigen specific CART-cells and untransduced CD4/CD8 T-cells demonstrated significant chemotaxis at multiple concentrations of CXCR3 agonist over DMSO control in a cell number dependent manner (FIG. 10A-C) (105,000 cell data shown in the picture).

Figure 10D:
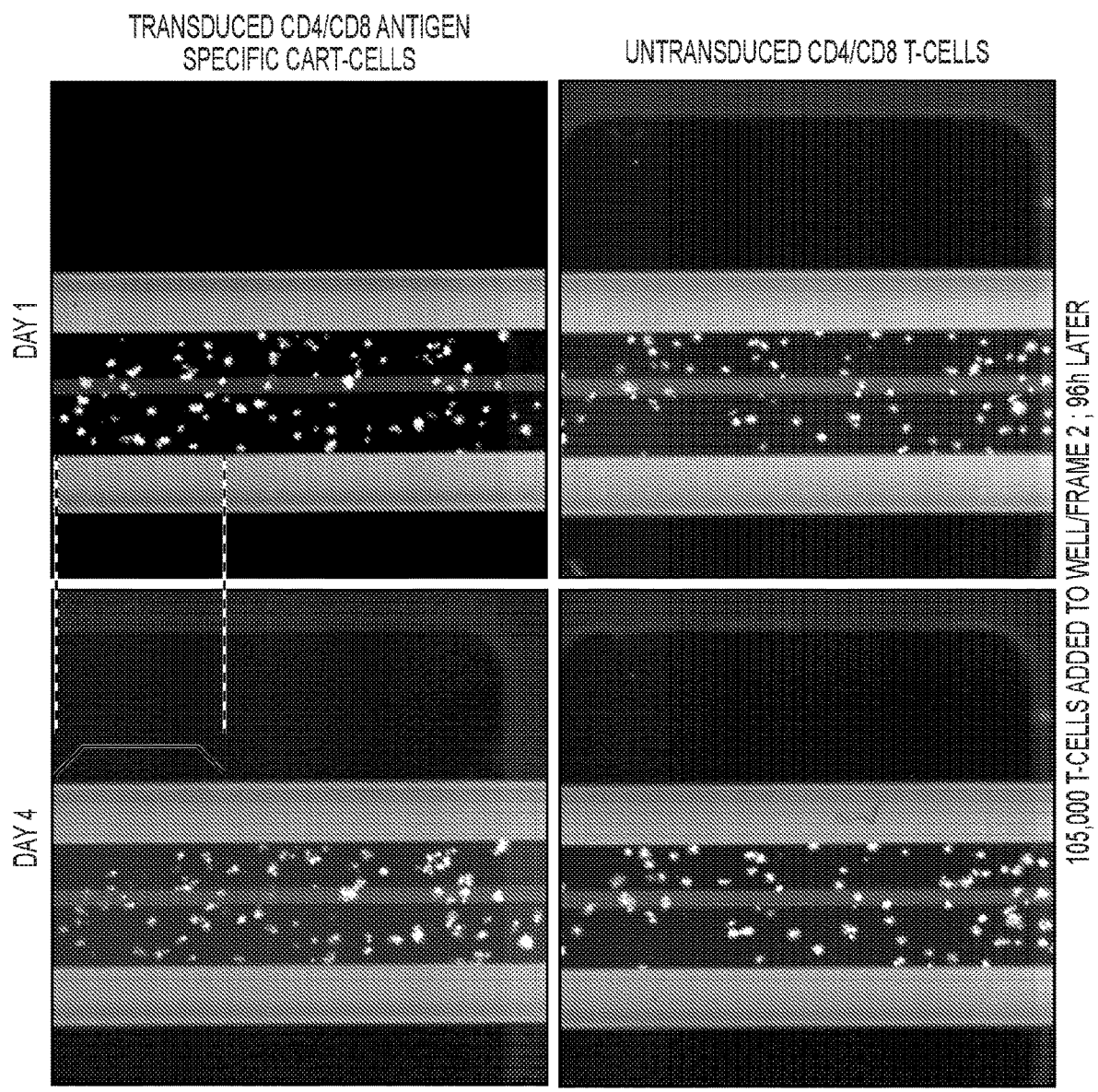
Figure 10E:
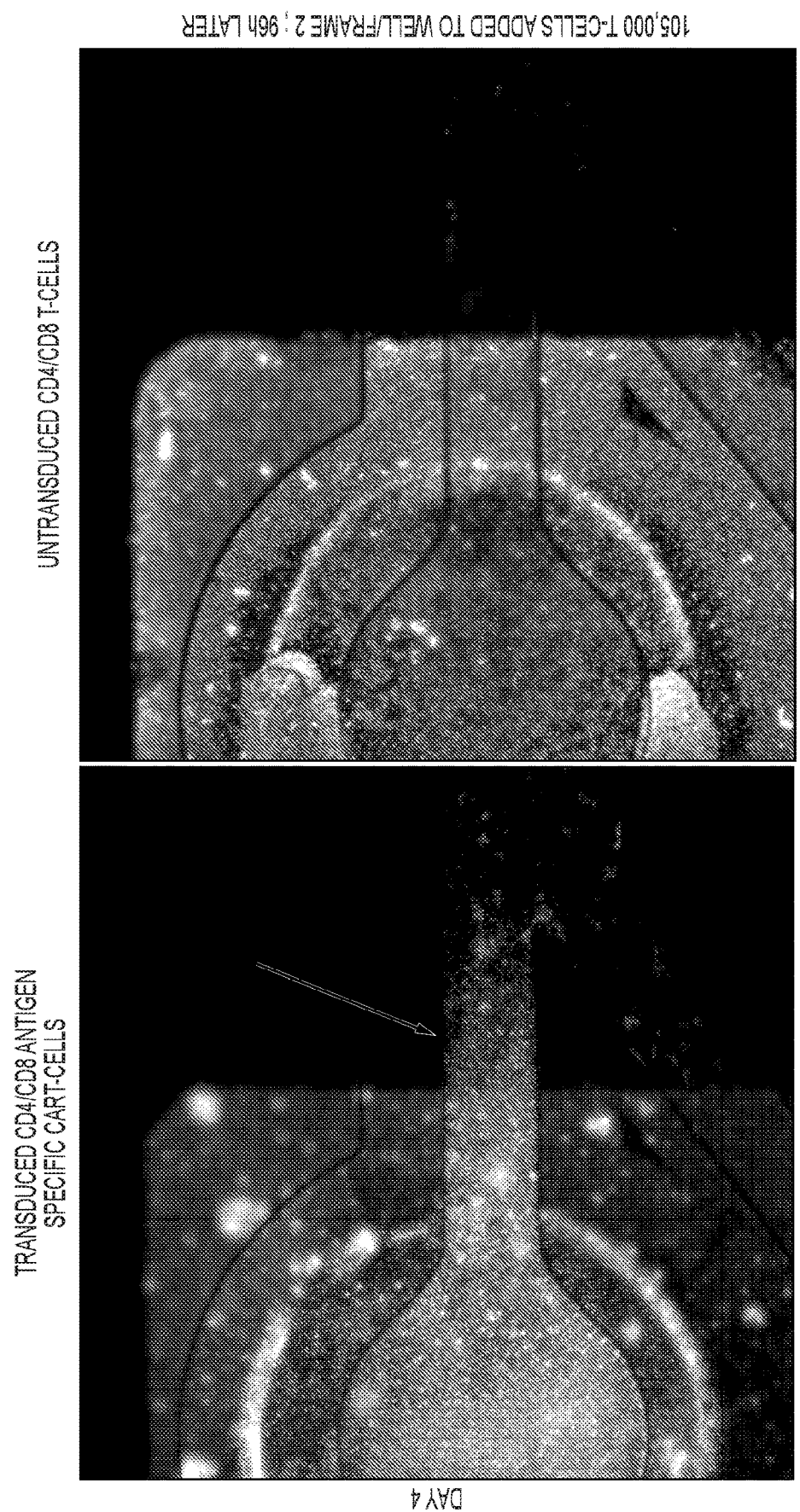

Addition of transduced CD4/CD8 antigen specific CART-cells to well/frame 2 (102) of two-day old 1000-single cell HT29-GFP colorectal cancer colonies embedded extracellular matrix filled 2-lane Mimetas ORGANOPLATE® demonstrated migration of the CART cells into the cancer cell laden matrix coupled with significant killing compared to untransduced CD4/CD8 T-cell controls. This was evidenced by a reduction in GFP+ colonies and punctate shaped GFP+cell debris in the wells treated with transduced CD4/CD8 antigen specific CART-cells over the untransduced controls (FIG. 10D) (105,000 cell Day 1 vs Day 4 data shown). In this untreated DMSO control, we observed a significant migration of transduced CD4/CD8 antigen specific CART-cells into 1000-single cell HT29-GFP colorectal cancer colonies embedded extracellular matrix compared to untransduced CD4/CD8 T-cells cells (FIG. 10E). Subsequently, the cancer cell colonies killing was observed only in the antigen specific CART wells, indicating the functional activity of antigen specific CART cells in killing the antigen matched tumor cell colonies in comparison to the untreated control T-cells (FIG. 10D).

REFERENCES

The disclosure of each reference cited is expressly incorporated herein.
1. Jin, T.; Xu, X.; Hereld, D. Chemotaxis, chemokine receptors and human disease. Cytokine 2008, 44, 1-8.
2. Kay, R. R.; Langridge, P.; Traynor, D.; et al. Changing directions in the study of chemotaxis. Nature reviews Molecular cell biology 2008, 9, 455-463.
3. Luster, A. D. Chemotaxis: role in immune response. e LS 2001.
4. Mackay, C. R. Chemokine receptors and T cell chemotaxis. The Journal of experimental medicine 1996, 184, 799-802.
5. Van Haastert, P. J.; Devreotes, P. N. Chemotaxis: signalling the way forward. Nature reviews Molecular cell biology 2004, 5, 626-634.
6. Manes, S.; Gómez-Moutón, C.; Lacalle, R. A.; et al. In Mastering time and space: immune cell polarization and chemotaxis, Seminars in immunology, Elsevier: 2005; pp 77-86.
7. Engelhardt, B. Immune cell entry into the central nervous system: involvement of adhesion molecules and chemokines. Journal of the neurological sciences 2008, 274, 23-26.
8. Jöhrer, K.; Pleyer, L.; Olivier, A.; et al. Tumour-immune cell interactions modulated by chemokines. Expert opinion on biological therapy 2008, 8, 269-290.
9. Luther, S. A.; Cyster, J. G. Chemokines as regulators of T cell differentiation. Nature immunology 2001, 2, 102-107.
10. Moser, B. Chemokines: role in immune cell traffic. European cytokine network 2003, 14, 204-210.
11. Nagarsheth, N.; Wicha, M. S.; Zou, W. Chemokines in the cancer microenvironment and their relevance in cancer immunotherapy. Nature Reviews Immunology 2017, 17, 559-572.
12. W Zimmermann, H.; Tacke, F. Modification of chemokine pathways and immune cell infiltration as a novel therapeutic approach in liver inflammation and fibrosis. Inflammation & Allergy-Drug Targets (Formerly Current Drug Targets-Inflammation & Allergy)(Discontinued) 2011, 10, 509-536.
13. Ponath, P. D.; Wang, J.; Heath, H. Transwell chemotaxis. In Chemokine Protocols; Springer: 2000, pp. 113-120.
14. Luster, A. D.; Alon, R.; von Andrian, U. H. Immune cell migration in inflammation: present and future therapeutic targets. Nature immunology 2005, 6, 1182-1190.
15. Moreau, H. D.; Piel, M.; Voituriez, R.; et al. Integrating physical and molecular insights on immune cell migration. Trends in immunology 2018, 39, 632-643.
16. Satti, S.; Deng, P.; Matthews, K.; et al. Multiplexed end-point microfluidic chemotaxis assay using centrifugal alignment. Lab on a Chip 2020, 20, 3096-3103.
17. Sai, J.; Rogers, M.; Hockemeyer, K.; et al. Study of chemotaxis and cell-cell interactions in cancer with microfluidic devices. Methods in enzymology 2016, 570, 19-45.
18. Zhang, C.; Barrios, M. P.; Alani, R. M.; et al. A microfluidic transwell to study chemotaxis. Experimental cell research 2016, 342, 159-165.
19. Bao, J.; Zhu, J.; Luo, S.; et al. CXCR7 suppression modulates microglial chemotaxis to ameliorate experimentally-induced autoimmune encephalomyelitis. Biochemical and biophysical research communications 2016, 469, 1-7.
20. Yao, J.; Harvath, L.; Gilbert, D.; et al. Chemotaxis by a CNS macrophage, the microglia. Journal of neuroscience research 1990, 27, 36-42.
21. Honda, S.; Sasaki, Y.; Ohsawa, K.; et al. Extracellular ATP or ADP induce chemotaxis of cultured microglia through Gi/o-coupled P2Y receptors. Journal of Neuroscience 2001, 21, 1975-1982.
22. O'Boyle, G.; Swidenbank, I.; Marshall, H.; et al. Inhibition of CXCR4-CXCL12 chemotaxis in melanoma by AMD11070. British journal of cancer 2013, 108, 1634-1640.
23. Van Duinen, V.; Van Den Heuvel, A.; Trietsch, S.; et al. 96 perfusable blood vessels to study vascular permeability in vitro. Scientific reports 2017, 7, 1-11.

24. Vormann, M. K.; Gijzen, L.; Hutter, S.; et al. Nephrotoxicity and kidney transport assessment on 3D perfused proximal tubules. The AAPS journal 2018, 20, 1-11.
25. Boppart, S. A., S. You, L. Li, J. Chen2, and H. Tul, Simultaneous label-free autofluorescence-multiharmonic microscopy and beyond. APL Photonics 4, 100901 (2019).

Additional Embodiments/Clauses

1. A method of preparing assay plates, comprising the steps of:
    filling a first channel of a first two-channel microfluidics unit with a fluid mixture of collagen and extracellular matrix to create aligned collagen fibers within the first channel;
    filling a second channel of the two-channel microfluidics unit with fluid extracellular matrix, thereby establishing fluid contact between the two channels;
    incubating the two-channel microfluidics unit until the extracellular matrix has formed a gel.
2. The method of any preceding clause wherein the fluid extracellular matrix is ice-chilled.
3. The method of any preceding clause wherein the step of incubating is performed at 37° C.
4. The method of any preceding clause wherein the first channel comprises a well at each end and the second channel comprises a well at one end, wherein the first and second channels are in fluid communication over a distance, wherein the fluid communication is distal to the well of the second channel.
5. The method of any preceding clause further comprising the step of adding an amount of test substance to the well of the first channel that is distal to the well of the second channel.
6. The method of any preceding clause further comprising the step of adding media with less than the amount or no test substance to the well of the second channel.
7. The method of any preceding clause further comprising the step of adding cells to the well of the first channel which is proximal to the well of the second channel.
8. The method of any preceding clause wherein the test substance a chemoattractant.
9. The method of any preceding clause wherein the test substance is a chemokine.
10. The method of any preceding clause wherein the first two-channel microfluidics unit is on a plate with a plurality of such units.
11. The method of any preceding clause wherein the two-channel microfluidics unit is on a plate with 96 of such units.
12. The method of claim 10 or 11 wherein the plurality of such units are filled by the method used for filling said first two-channel microfluidics unit.
13. An assay plate made by the process of any of clauses 1 to 12.
14. An assay plate for assaying chemotaxis of a cell population, said assay plate comprising:
    a first two-channel microfluidics unit comprising a first channel and a second channel, wherein the first channel comprises a first gel, wherein the second channel comprises a second gel, wherein the first and second channels are in fluid communication over a central window.
15. The assay plate of clause 14 wherein the first and second channels are in fluid communication over a distance in which they are parallel.
16. The assay plate of any of clauses 14 or 15 wherein the first channel comprises a well at each end and the second channel comprises a well at one end, wherein the first and second channels are in fluid communication over a central window that is distal to the well of the second channel.
17. The assay plate of any of clauses 14 to 16 that comprises a plurality of two-channel microfluidics units.
18. The assay plate of any of clauses 14 to 17 that comprises 96 two-channel microfluidics units.
19. The assay plate of any of clauses 14 to 18 wherein the first gel and the second gel comprise extracellular matrix.
20. The assay plate of any of clauses 14 to 19 wherein the first gel comprises collagen.
21. The assay plate of any of clauses 14 to 20 wherein the first gel comprises aligned collagen fibers.
22. A method of assaying chemotaxis of a cell population, comprising:
    (1) providing an assay plate comprising a first two-channel microfluidics unit comprising a first channel and a second channel, wherein the first channel comprises a first gel; wherein the second channel comprises a second gel, wherein the first channel comprises a well at each end and the second channel comprises a well at one end, wherein the first gel in the first channel extends between wells at each end, wherein the second gel in the second channel extends from the well at one end through a central window in which the first and second channels are in fluid communication over a distance; wherein the central window is distal to the well of the second channel;
    (2) adding a population of cells to a well of the assay plate, wherein the well is at one end of the first channel and the well is proximal to the well of the second channel;
    (3) adding a fluid medium to the well of the second channel and to the distal well of the first channel;
    (4) adding a test substance to the distal well of the first channel; and,
    (5) monitoring location of the cells of the population within the central window as the cells traverse the first channel from the well containing the cells toward the well containing the test substance, wherein the monitoring comprises using Simultaneous Label-free Autofluorescence Multi-harmonic imaging (SLAM) detecting one or more of the following: collagen, nicotinamide adenine dinucleotide (NAD), and flavin adenine dinucleotide (FAD).

We claim:
1. A method of assaying chemotaxis of a cell population, comprising:
    providing an assay plate comprising a first two-channel microfluidics unit comprising a first channel and a second channel, wherein the first channel comprises a first gel; wherein the second channel comprises a second gel, wherein the first channel comprises a well at each end and the second channel comprises a well at one end, wherein the first gel in the first channel extends between wells at each end, wherein the second gel in the second channel extends from the well at one end through a central window in which the first and second channels are in fluid communication over a distance; wherein the central window is distal to the well of the second channel;

adding a population of cells to a well of the assay plate, wherein the well is at one end of the first channel and the well is proximal to the well of the second channel;

adding a fluid medium to the well of the second channel and to the distal well of the first channel;

adding a test substance to the distal well of the first channel;

monitoring location of the cells of the population within the central window as the cells traverse the first channel from the well containing the cells toward the well containing the test substance.

2. The method of claim 1 wherein the test substance is an agonist of a chemoattractant receptor.

3. The method of claim 1 wherein the test substance is a chemoattractant.

4. The method of claim 1 wherein the test substance is an antagonist of a chemoattractant.

5. The method of claim 1 wherein the population of cells are immune cells.

6. The method of claim 1 wherein the population of cells are T cells.

7. The method of claim 1 wherein the population of cells are a subset of T cells selected from the group consisting of CD4+ T cells, CD8+ T cells, regulatory T (Treg) cells, T follicular helper (Tfh) cells, naïve T cells, memory T cells, Th1 cells, Th2 cells, Th17 cells, and activated T cells.

8. The method of claim 1 wherein the monitoring measures speed of cell migration.

9. The method of claim 1 wherein the monitoring measures distance of cell migration.

10. The method of claim 1 wherein the monitoring utilizes confocal microscopy.

11. The method of claim 1 wherein the assay plate is not rocked before or during the monitoring.

12. The method of claim 1 wherein the assay plate comprises a plurality of two-channel microfluidic units, wherein different test substances are added to different distal wells of the first channels of different two-channel microfluidic units.

13. The method of claim 12 wherein the different test substances are provided by different cell populations that make the test substances in situ.

14. The method of claim 1 further comprising the step of identifying a test substance as a chemoattractant.

15. The method of claim 1 wherein a known chemoattractant in addition to the test substance is added to the distal wells of the first channels.

16. The method of claim 1 further comprising the step of identifying an agonist of the chemoattractant receptor.

17. The method of claim 1 further comprising the step of identifying an antagonist of the chemoattractant.

18. The method of claim 1 wherein the assay plate comprises a plurality of two-channel microfluidic units, wherein different types of populations of cells are added to different proximal wells of the first channels of different two-channel microfluidic units.

19. The method of claim 1 wherein the assay plate comprises a plurality of two-channel microfluidic units, wherein different concentrations of test substances are added to different distal wells of the first channels of different two-channel microfluidic units.

20. The method of claim 1 wherein the assay plate comprises a plurality of two-channel microfluidic units, wherein different concentrations of the test substance are added to the well of the second channel of different two-channel microfluidic units to create different gradients of the test substance in different two-channel microfluidic units.

21. The method of claim 1 wherein the assay plate comprises a plurality of two-channel microfluidic units, wherein populations of cells previously subjected to different treatments are added to different proximal wells of the first channels of different two-channel microfluidic units.

22. The method of claim 1 further comprising the step of identifying a cell population that makes a chemoattractant.

23. The method of claim 1 wherein the first gel and the second gel comprise extracellular matrix.

24. The method of claim 1 wherein the first gel comprises collagen.

25. The method of claim 1 wherein the first gel comprises aligned collagen fibers.

* * * * *